United States Patent
Combier et al.

(10) Patent No.: US 10,920,236 B2
(45) Date of Patent: Feb. 16, 2021

(54) USE OF MICROPEPTIDES IN ORDER TO STIMULATE MYCORRHIZAL SYMBIOSIS

(71) Applicants: UNIVERSITE TOULOUSE III—PAUL SABATIER, Toulouse (FR); CENTRE NATIONAL DE LA RECHERCHE SCIENTIFIQUE, Paris (FR)

(72) Inventors: Jean-Philippe Combier, Castanet Tolosan (FR); Dominique Lauressergues, Toulouse (FR); Guillaume Becard, Odars (FR)

(73) Assignees: UNIVERSITE TOULOUSE III—PAUL SABATIER, Toulouse (FR); CENTRE NATIONAL DE LA RECHERCHE SCIENTIFIQUIE, Paris (FR)

( * ) Notice: Subject to any disclaimer, the term of this patent is extended or adjusted under 35 U.S.C. 154(b) by 65 days.

(21) Appl. No.: 15/315,472

(22) PCT Filed: Jun. 3, 2015

(86) PCT No.: PCT/FR2015/051473
§ 371 (c)(1),
(2) Date: Dec. 1, 2016

(87) PCT Pub. No.: WO2015/185862
PCT Pub. Date: Dec. 10, 2015

(65) Prior Publication Data
US 2017/0253884 A1 Sep. 7, 2017

(30) Foreign Application Priority Data

Jun. 3, 2014 (FR) .................................. 14 55047
Mar. 24, 2015 (FR) .................................. 15 52462

(51) Int. Cl.
| | | |
|---|---|---|
| C12N 15/82 | (2006.01) |
| C07K 14/415 | (2006.01) |
| C12N 15/11 | (2006.01) |
| A01H 3/04 | (2006.01) |
| A01N 37/46 | (2006.01) |
| C12N 1/14 | (2006.01) |

(52) U.S. Cl.
CPC ........... *C12N 15/8216* (2013.01); *A01H 3/04* (2013.01); *A01N 37/46* (2013.01); *C07K 14/415* (2013.01); *C12N 1/14* (2013.01); *C12N 15/111* (2013.01); *C12N 15/8218* (2013.01); *C12N 15/8241* (2013.01); *C12N 15/8261* (2013.01); *C12N 15/8271* (2013.01); *C12N 15/8273* (2013.01); *C12N 2310/141* (2013.01); *Y02A 40/146* (2018.01)

(58) Field of Classification Search
None
See application file for complete search history.

(56) References Cited

FOREIGN PATENT DOCUMENTS

FR 1360727 A1 10/2013

OTHER PUBLICATIONS

Sequence Accession AZH78273, dated Jun. 23, 2011, sequence alignment provided in the Office Action (Year: 2011).*
Xue, X. et al., "Interaction Between Two Timing MicroRNAs Controls Trichome Distribution in *Arabidopsis*," PLOS Genetics, vol. 10, No. 4, Apr. 3, 2014, pp. 1-13.
Lauressergues, D. et al., "The MicroRNA miR17h Modulates Arbuscular Mycorrhizal Colonization of Medicago Truncatula by Targeting NSP2," The Plant Journal, vol. 72, No. 3, Aug. 30, 2012, pp. 512-522.
Bari, A et al., "miR156- and miR171-Binding Sites in the Protein-Coding Sequences of Several Plant Genes," Biomed Research International, 2013, pp. 1-8.
Sunkar, R. et al., "Identification of Novel and Candidate miRNAs in Rice by High Throughput Sequencing," BMC Plant Biology, vol. 8, No. 1, Feb. 29, 2008, pp. 1-17.
Bardou, F. et al., "Dual RNAs in Plants," Biochimie, vol. 93, No. 11, Nov. 1, 2011, pp. 1950-1954.
Crappe, J. et al., "Little Things Make Big Things Happen: A Summary of Micropeptide Encoding Genes," EUPA Open Proteonomics, vol. 3, Jun. 1, 2014, pp. 128-137.
De Coninck, B. et al., "Mining the Genome of *Arabidopsis thaliana* as a Basis for the Identification of Novel Bioactive Peptides Involved in Oxidative Stress Tolerance," Journal of Experimental Botany, vol. 64, No. 17, Dec. 1, 2013, pp. 5297-5307.
Engstrom, E., "HAM Proteins Promote Organ Indeterminacy," Plant Signaling & Behavior, vol. 7, No. 2, Feb. 2012, pp. 1-8.
Stuurman, J. et al., "Shoot Meristem Maintenance is Controlled by a GRAS-Gene Mediated Signal from Differentiating Cells," Genes & Development, vol. 16, 2002, pp. 2213-2218.
International Search Report issued in International Application No. PCT/FR2015/051473, dated Sep. 17, 2015 with English Translation.
Written Opinion issued in International Application No. PCT/FR2015/051473, dated Dec. 6, 2016.
Preliminary Search Report issued in French Application No. FR 1455047, dated Feb. 9, 2015.

* cited by examiner

*Primary Examiner* — Elizabeth F McElwain
(74) *Attorney, Agent, or Firm* — Maier & Maier, PLLC

(57) ABSTRACT

A method for promoting mycorrhizal symbiosis between a plant and a fungus includes using micropeptides (peptides encoded by microRNAs or "miPEPs").

Figure 1:
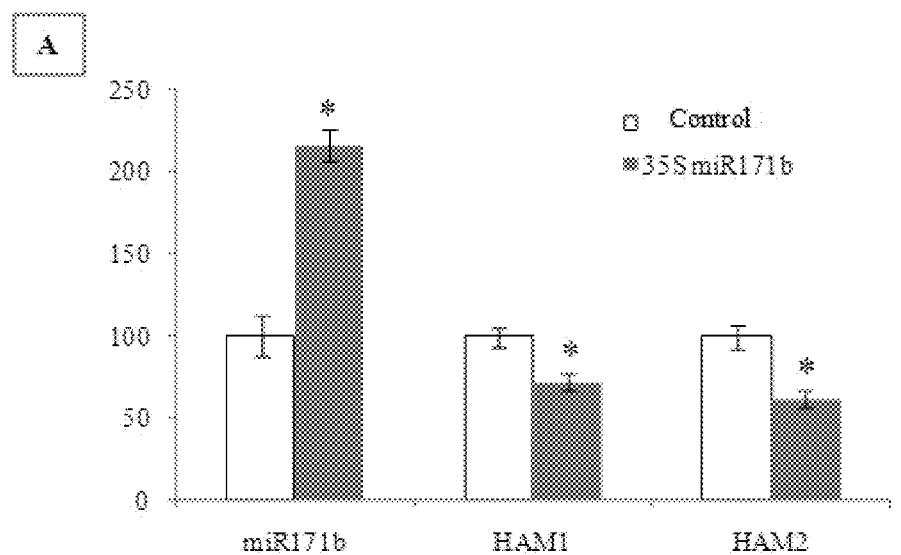
Figure 1:
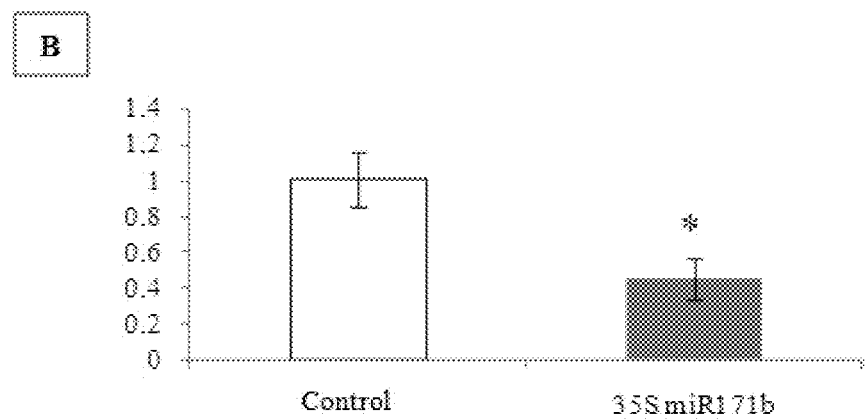

16 Claims, 11 Drawing Sheets
Specification includes a Sequence Listing.

SEQUENCE LISTING

```
<160> NUMBER OF SEQ ID NOS: 16

<210> SEQ ID NO 1
<211> LENGTH: 21
<212> TYPE: RNA
<213> ORGANISM: Medicago truncatula

<400> SEQUENCE: 1
ugauugagcc gcgucaauau c                                            21

<210> SEQ ID NO 2
<211> LENGTH: 20
<212> TYPE: PRT
<213> ORGANISM: Medicago truncatula

<400> SEQUENCE: 2

Met Leu Leu His Arg Leu Ser Lys Phe Cys Lys Ile Glu Arg Asp Ile
1               5                   10                  15

Val Tyr Ile Ser
            20

<210> SEQ ID NO 3
<211> LENGTH: 63
<212> TYPE: DNA
<213> ORGANISM: Medicago truncatula

<400> SEQUENCE: 3
atgcttcttc ataggctctc caaattttgc aaaattgaaa gaggcatagt atatatatct    60
tag                                                                 63

<210> SEQ ID NO 4
<211> LENGTH: 728
<212> TYPE: DNA
<213> ORGANISM: Medicago truncatula

<400> SEQUENCE: 4
attggtcaaa catacataca gtagcactag ctggtttcat tattccacta tgcttcttca    60
taggctctcc aaattttgca aaattgaaag aggcatagta tatatatctt agcaaggaga   120
aattcaggat attgaggatg aagattgaag agtaatcagt gatgaagaaa gcaagcaagg   180
tattggcgcg cctcaatttg aatacatggc tataaaaatg catcatatca gccatgtagt   240
ttgattgaac cgcgtcaata tcttgtttcc atctccaaat ttaccaatct catcaaatca   300
aattaacacc acaatcaagt caaaataggt tgaccttatc atcgaagaaa ttgttttctc   360
attcctatcg aagttggact tgctgaaaat gctcgaaagc atgtgtttta gttcgacagg   420
```

```
cgaaaaagtt accgaaggac aatttggttg tggttcggat aaggtcaagc aacggatatt      480
ttcaagacac gttcgaaatt caagtcaaat ggataagtat cgttagttta ctgcagttat      540
agttttaaat tcaaatctag gcagttattt ctatttgtat aaatagtagt ttttccctag      600
ggaaaaaggg tcgcaattca atcatacaaa aaacttacaa tcaaattatc cgcatggaag      660
agagaaacga gtcacaagtt gcaatgtatg aacatgtgta ccaatttaca ttcaatcagt      720
acaatttt                                                               728

<210> SEQ ID NO 5
<211> LENGTH: 21
<212> TYPE: RNA
<213> ORGANISM: Solanum lycopersicum

<400> SEQUENCE: 5
uugagccgcg ucaauaucuc u                                                21

<210> SEQ ID NO 6
<211> LENGTH: 19
<212> TYPE: PRT
<213> ORGANISM: Solanum lycopersicum

<400> SEQUENCE: 6

Met Lys Leu Gly Asn Ile Glu Gly Thr Tyr Phe Ile Ile Cys Leu Gly
1               5                   10                  15

Arg Tyr Ile

<210> SEQ ID NO 7
<211> LENGTH: 60
<212> TYPE: DNA
<213> ORGANISM: Solanum lycopersicum

<400> SEQUENCE: 7
atgaagttgg gaaatattga aggtacgtac tttataatat gtttaggaag atatatatag       60

<210> SEQ ID NO 8
<211> LENGTH: 1000
<212> TYPE: DNA
<213> ORGANISM: Solanum lycopersicum

<400> SEQUENCE: 8
gtctttgagg gcatgaatag tgtaatatgg acccattcgt gtgtggaaaa attgtacaat       60
attccaagaa aaacgtacc tgtccacatt aattagttag gtaagtggat tatactactc      120 ataaatatt atattacagc caaggaatc caacttctct aaaataaaaa taaaaaacac       180
caaattaatg tttgtttcaa tattttgatg tacattactt tagagcaagt attagcaaga      240
tacattaggc tatttttgt ttttcggaa tcacatcaag aaatgaaaga tctttggtca      300
caacatgatg aagatacata gttgaaactt gaaagatata atagttttga tttttcgtat      360
tgaaaattat tctgcaaatt gatggatagc tagctaattc aaagatgaag ttgggaaata      420
ttgaaggtac gtactttata atatgtttag gaagatatat atagatattg atgcggttca      480
atctgaaaga catggttaga tatgtaatta gccttgtaat tttggattga gccgcgtcaa      540
tatctctctt cctattttca attagtttat aagtaacttg aactttattt aattactcgt      600
tggtaatact tgtcttgttt catgttttcc tcttggccat gcatctttaa tgtttttttt      660
tccactaatt ttctggtttt taattagttt ttaaatttct tcttaatttc atctttgaca      720
ccattaattt cattcgttgc cgttcgttga tagacgtttt tgaattagat agttaatcat      780
```

```
aattaataca tgaatgaatc gatcaagagc tagcatggaa attaatgatt gtgttgaatg      840 atttttttt gtattatttt ttgcttctta aggtaattgc aacctacttt tgcttatata      900
ttttctttta ttatttgaat ttcgaggtat tttcactacc tcaaataatt accttctttc      960
ctgatttcaa ttttctttca taaaaaagcg tctttctaaa                           1000
```

<210> SEQ ID NO 9
<211> LENGTH: 21
<212> TYPE: RNA
<213> ORGANISM: Lotus japonicus

<400> SEQUENCE: 9

```
ugauugagcc gcgucaauau c                                               21
```

<210> SEQ ID NO 10
<211> LENGTH: 22
<212> TYPE: PRT
<213> ORGANISM: Lotus japonicus

<400> SEQUENCE: 10

```
Met Tyr His Arg Ser Lys Ala Lys Leu Cys Gln Thr Asp Gly Asp Asp
1               5                   10                  15

Gly Gly Gly Ser Asp Met
            20
```

<210> SEQ ID NO 11
<211> LENGTH: 69
<212> TYPE: DNA
<213> ORGANISM: Lotus japonicus

<400> SEQUENCE: 11

```
atgtatcatc gaagcaaagc aaaactatgt caaactgatg gtgatgatgg aggaggaagt      60
gatatgtga                                                             69
```

<210> SEQ ID NO 12
<211> LENGTH: 1220
<212> TYPE: DNA
<213> ORGANISM: Lotus japonicus

<400> SEQUENCE: 12

```
gagaaataca aaaacccaac aaaacccaac tcaaatatat attctccacc aagcagaaac      60
cagatttcat ctcgttacag tatcaccata gtccacgccc aactccaaaa gccatgccac     120
aagccaaaac aaaacgtcag gtacagatca caggacaaaa tagcttttt ccaatcagcc      180 caagtataca aagcaaagat gatataaagt ggtccatgat ggtgggtgta attcgtatta     240
acaacttaat taatatgtac attaatgtac catctaacgg gtatatggaa attcagtctc     300
tttcatgacc ttatatttcg cctcaatgcc tcattatagg catccatcca tgcagatgaa     360
attccaataa caacctcccc gtcttaattc aattgagaca atattttgtt gggatttgca     420
aggcacttag aaaataattt ttgaaacaca acaaagcca cttgatagag tcatagaggt      480
agtagaacag aaacacttgg cgattgagtt ttgttttttt aaagtatttt tcgaaattga     540
ggaggaaaac taattaatat ttgcgctcat tcgtgggaaa agtggtcgtt ggtcaaagag     600
tcgcacaaat attatttcag cacttgtggt ttggtttaat ggttttgatg aattcattcc     660
actttgctta ttccccccagt ctgcaacaca aaatgatgtg ttttccaaaa ttaaagacag     720
atctcaaaag caggtgttag ttaatttcct catgtatcat cgaagcaaag caaaactatg     780
tcaaactgat ggtgatgatg gaggaggaag tgatatgtga agcacaaatt aacaaggtat     840
```

```
tgacgcgtct caatttgaag acatggctgg ctaacatgaa aaccaatcat gtagtttgat    900
tgagccgcgt caatatcttg cttttgcgta cttctttcca tgtccatctg gccaccaatc    960
tcaactcaaa cgcccaccgg tatgtataat cattattgaa tgcttaattg tgttctctta   1020
attttgtata atctatattc atagtactgt ttctcttttct gcagaaaatc aaaatgcgtt   1080
atacatcaga agtaggtaaa attgacgtat caggtcagcc atcacagctt gcaccaatca   1140
ttattatatt gtattatctg atatgcacaa attaatggaa attataaaat cctttaaatg   1200
gtatagtata ggtgtggaaa                                               1220

<210> SEQ ID NO 13
<211> LENGTH: 21
<212> TYPE: RNA
<213> ORGANISM: Oryza sativa

<400> SEQUENCE: 13
ggauugagcc gcgucaauau c                                               21

<210> SEQ ID NO 14
<211> LENGTH: 31
<212> TYPE: PRT
<213> ORGANISM: Oryza sativa

<400> SEQUENCE: 14

Met Ile Ala Arg Tyr Ile Glu Arg Glu Met Thr Ser Lys Leu Gly Arg
1               5                   10                  15

Gly Arg Lys Arg Ala Ala Arg Leu Val Ala Val Phe Leu Leu Gly
            20                  25                  30

<210> SEQ ID NO 15
<211> LENGTH: 96
<212> TYPE: DNA
<213> ORGANISM: Oryza sativa

<400> SEQUENCE: 15
atgatagcta gatatatcga gagggagatg accagtaagc ttggaagagg aagaaagaga     60
gctgctaggc ttgttgcggt cttttttgctt gggtaa                              96

<210> SEQ ID NO 16
<211> LENGTH: 790
<212> TYPE: DNA
<213> ORGANISM: Oryza sativa

<400> SEQUENCE: 16
agaagaatgg ttgtgattga ttgagaggag gaggtaggtg aagaaatagc ttcattttag     60
gacaagacac tgtgctaaaa atagctatat tttaggacgg agagagtaga taagctagtc    120 ccgaccccc tcctctcctc tcttgccccg cctatataat ccccaaacat cgctttctct    180
tggagtagga aagggtagt agtttaagct atagctctaa agcatcacc atgcaacatt     240 acttgcgtta ttactatacc tatccaccac ctacacattt tgtcatctcc ctctctcttt    300
ctctctgatc tgtctcagat gtttatgcac atatacaagt taatagttct gtggatctag    360
caatcccggc ttgtttgttt ttgctgcttt ggtttgatga tagctagata tatcgagagg    420
gagatgacca gtaagcttgg aagaggaaga aagagagctg ctaggcttgt tgcggtcttt    480
ttgcttgggt aaaaagaggt attggcgtgc ctcaatccga aggcatggct gattacaggc    540
acctcgaccg atctagcgca tgcagccatg tttcttggat tgagccgcgt caatatctct    600
```

```
ccttgcttcc ttacttcatg tactgtgtca tgctcaagca tatgtcccct ctccgatctt    660
cctacctcgt cgagttcgtc ggatcagttc ccaaattaaa ggtgttatat atatatatat    720
atatatatat atatatatat atatatatat atatatatag taaatttgtt tggtgctcca    780
tggtgcccgg                                                           790
```

USE OF MICROPEPTIDES IN ORDER TO STIMULATE MYCORRHIZAL SYMBIOSIS

The present invention relates to the use of micropeptides (peptides encoded by microRNAs or "miPEPs") for promoting mycorrhizal symbiosis between a plant and a fungus.

Mycorrhizal symbiosis is an ancient biological process and is frequent in nature. The arbuscular mycorrhizal symbiosis (AM) in fact dates back more than 400 million years, and associates most terrestrial plants and glomeromycetes fungi. This symbiosis improves the hydric and mineral nutrition of the plants, but also their resistance to different biotic and abiotic stresses.

In general, the mycorrhizal fungi, which are incapable of photosynthesis, are dependent on the plant that they colonize in order to recover carbon-containing substances. In return, the mycorrhizal fungi supply the plant with mineral substances and water that they are capable of capturing in the soil.

Mycorrhizal symbioses can therefore benefit the growth and the protection of the plants against various biotic and abiotic stresses. Mycorrhizal symbiosis can also stimulate plant growth, while considerably reducing the requirement of crops for fertilizer. Furthermore, the mycelium constitutes an extension of the root system of the plants which allows the latter to better exploit the water and the minerals in an increased volume of soil. Such plants, better nourished and in better health, have greater resistance to environmental stresses such as drought, and survive pathogen attacks better.

MicroRNAs (miRNAs) are small non-encoding RNAs, of about 21 nucleotides after maturation, which control the expression of target genes at the post-transcriptional level, by degrading the target mRNA or inhibiting translation thereof. MiRs are in particular found in plants.

The genes targeted by the miRNAs are often key genes in developmental processes. For example, miR171b targets transcription factors of the GRAS family, specific to plants, which are known for their involvement in the functions of the meristems (Stuurman et al., *Genes Dev,* 16:2213-8, 2002; Engstrom et al., *Plant Signal Behav,* 20116:850-4). Moreover, this family comprises key genes regulating root development, such as the Scarecrow and Shortroot genes.

As mycorrhization is closely linked to root development, it has moreover been demonstrated recently that the miR171h regulates arbuscular mycorrhization in *Medicago truncatula* by means of negative regulation of the NSP2 gene, limiting the over colonization of the roots by the mycorrhizal fungi (Lauressergues et al., *Plant journal,* 75:512-22, 2012).

Very little is known about regulation of the expression of miRNAs, but it has been demonstrated that the latter involves, like most encoding genes, an RNA polymerase II: this enzyme produces a primary transcript, called "pri-miRNA", which is then matured by a protein complex containing in particular enzymes of the Dicer type. This maturation leads firstly to formation of a miRNA precursor called "pre-miRNA", having a secondary structure of stem-loop form containing the miRNA and its complementary sequence miRNA*. Then the precursor is matured, which leads to formation of a shorter double-stranded RNA containing the miRNA and the miRNA*. The miRNA then comes under the control of the RISC complex, which cleaves the mRNA of the target gene or inhibits its translation.

To date, the miRNAs, and by extension their primary transcript, have always been regarded, on account of their particular mode of action, as non-encoding regulatory RNAs that do not produce any peptide. Now, the inventors have recently demonstrated, in patent application FR 13/60727, the existence of micropeptides (or "miPEPs", microRNA encoded PEPtides) capable of modulating the accumulation of miRNAs.

In this context, the purpose of the present invention is to propose novel, effective and environmentally friendly tools for promoting the symbiosis between a plant and a fungus.

An aspect of the invention is to propose a novel use of miPEPs for promoting mycorrhizal symbiosis between a plant and a fungus.

Another aspect of the invention also relates to a novel method of growing plants in symbiosis with a fungus.

Another aspect of the invention is to propose a miPEPs composition making it possible to promote mycorrhizal symbiosis between a plant and a fungus.

One of the other aspects of the invention is also to propose a transgenic plant and parts of transgenic plants, and the method for the production thereof.

One of the other aspects of the invention is also to propose organs, cells and seeds of transgenic plants.

One of the other aspects of the invention is to propose ecologically modified plants.

One of the other aspects of the invention is to propose inocula of mycorrhizal fungi.

The invention therefore relates to the use of a peptide for promoting mycorrhizal symbiosis between a plant and a fungus, and in particular arbuscular mycorrhizal symbiosis (AM), said peptide being introduced into the plant, said peptide having an amino acid sequence comprising or consisting of a sequence identical to that of a miPEP naturally present in said plant, said miPEP naturally present in said plant being a peptide of 3 to 100 amino acids, in particular of 4 to 100 amino acids, the sequence of which is encoded by an open reading frame situated on the primary transcript of a miRNA, said miPEP being capable of modulating the accumulation of said miRNA in said plant, which miRNA regulates the expression of at least one gene involved in the mycorrhizal symbiosis in said plant.

Surprisingly and unexpectedly, the inventors found that the use of peptides the sequence of which comprises or consists of a sequence identical to that of miPEPs encoded on the primary transcripts of miRNAs, makes it possible to promote mycorrhizal symbiosis between a plant and a fungus.

In the invention, the terms "microRNA", "non-encoding microRNA" and "miRNA" are equivalent and may be used interchangeably. They define small RNA molecules of about 21 nucleotides, which are not translated and do not lead to a peptide or a protein. However, in this mature form, the miRNAs perform a function of regulation of certain genes by post-transcriptional mechanisms, for example via the RISC complex.

The "primary transcript of miRNA" (or "pri-miRNA") for its part corresponds to the RNA molecule directly obtained from transcription of the DNA molecule. Generally, this primary transcript undergoes one or more post-transcriptional modifications, which lead for example to a particular structure of the RNA or a cleavage of certain parts of the RNA by splicing phenomena, and which lead to the precursor form of the miRNA (or "pre-miRNA"), and then to the mature form of the miRNA.

The terms "micropeptides" and "miPEPs" (microRNA encoded PEPtides) are equivalent and may be used interchangeably. They define a peptide that is encoded by an open reading frame present on the primary transcript of a miRNA, and that is capable of modulating the accumulation of said miRNA. The miPEPs in the sense of the present invention must not be understood as necessarily being peptides of small size, as "micro" does not refer to the size of the peptide.

As stated in patent application FR 13/60727, the contents of which are to be regarded as forming part of the present application, the miPEPs are peptides:
from 4 to 100 amino acids, preferably from 4 to 60 amino acids, in particular of 4 to 59 amino acids,
encoded by an open reading frame contained in the primary transcript of a miRNA, preferably in the 5' part of the primary transcript of said miRNA, and
capable of modulating the accumulation of said miRNA in a eukaryotic cell.

The terms "open reading frame" or "ORF" are equivalent and may be used interchangeably. They correspond to a nucleotide sequence in a DNA or RNA molecule that may potentially code for a peptide or a protein: said open reading frame begins with a start codon (the start codon generally encoding for a methionine), followed by a series of codons (each codon encoding for an amino acid), and ends with a stop codon (the stop codon not being translated).

In the invention, the ORFs may be called specifically "miORFs" when the latter are present on the primary transcripts of miRNA.

The miORFs as defined in the invention may have a size from 15 to 303 nucleotides. As an amino acid is encoded by a codon of 3 nucleotides, the miORFs from 15 to 303 nucleotides code for miPEPS from 4 to 100 amino acids.

In particular, the miORFs have a size of:
15, 18, 21, 24, 27, 30, 33, 36, 39, 42, 45, 47, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, 156, 159, 162, 165, 168, 171, 174, 177, 180, 183, 186, 189, 192, 195, 198, 201, 204, 207, 210, 213, 216, 219, 222, 225, 228, 231, 234, 237, 240, 243, 246, 249, 252, 255, 258, 261, 264, 267, 270, 273, 276, 279, 282, 285, 288, 291, 294, 297, 300 or 303 nucleotides, and code respectively for miPEPs having a size of:
4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 amino acids.

A miPEP may also have a size of 3 amino acids.

Taking into account the degeneration of the genetic code, one and the same miPEP may be encoded by several nucleotide sequences. Such nucleotide sequences, differing from one another by at least one nucleotide but encoding for one and the same peptide, are called "degenerated sequences".

In the invention, the term "plant" refers generally to all or part of a plant whatever its stage of development (including the plant in the form of a seed or a young shoot), to one or more organs of the plant (for example the leaves, roots, stem, flowers), to one or more cells of the plant, or to a cluster of cells of the plant.

The expression "mycorrhizal symbiosis" refers to the symbiotic association between a mycorrhizal fungus and the roots of a plant. In the invention, this symbiotic association can also be called "mycorrhization".

The expression "arbuscular mycorrhizal symbiosis" refers to the symbiotic association between a glomeromycete fungus and a plant. The arbuscular mycorrhizal fungi are capable of penetrating into the roots of the plant and can form particular branched cellular structures in the plant cells. Such structures are called arbuscular due to their form which resembles that of a small tree.

Non-limitatively, the parameters making it possible to determine and quantify the mycorrhizal symbiosis between a plant and a fungus can be in particular:
the length and the number of roots of the plant,
the percentage colonization of a plant by the fungus,
the number, the size and the surface area of the arbuscules, or also the root or aerial growth of the mycorrhization.

Moreover, in the invention, the expression "promote the mycorrhizal symbiosis», or "improve the mycorrhizal symbiosis», indicates:
either an acceleration of the mycorrhization (such as for example a higher percentage colonization for a plant at a given time relative to a reference plant),
or an increase in the mycorrhization (such as for example a higher percentage colonization for a plant which is not affected relative to a reference plant grown under the same conditions),
or an acceleration of and an increase in the mycorrhization.

It is important to note that the use according to the invention has the advantage of being ecological, as the miPEP is a peptide which is naturally present in the plant.

The invention also relates to the use of a miPEP introduced exogenously in a plant in order to promote mycorrhizal symbiosis between said plant and a fungus, in particular the arbuscular mycorrhizal symbiosis,
said miPEP introduced exogenously being a peptide comprising, or consisting of, a sequence identical to that of a miPEP naturally present in said plant,
said miPEP naturally present is a peptide of 3 to 100 amino acids, in particular of 4 to 100 amino acids, the sequence of which is encoded by an open reading frame situated at 5' on the primary transcript of a miRNA,
said miPEP being capable of modulating the accumulation of said miRNA in said plant, which miRNA regulates the expression of at least one gene involved in the mycorrhizal symbiosis,
the sum of the quantity of said miPEP introduced exogenously and that of said miPEP naturally present being strictly greater than the quantity of present miPEP naturally present.

In the invention, the expression "miPEP introduced exogenously" refers to a miPEP introduced into the plant artificially, whether or not the latter is naturally present in the plant.

If the miPEP occurs naturally in the plant, it is an "miPEP of endogenous origin".

If the miPEP does not occur naturally in the plant, it is an "miPEP of exogenous origin". When an "miPEP of exogenous origin" is introduced into the plant, it is then also necessary to introduce the corresponding miRNA and its primary transcript.

Introduction of a miPEP exogenously into the plant therefore involves a technical step; said step is not a natural phenomenon and does not correspond to crossing or to selection.

The miPEP introduced exogenously may either be a peptide produced outside of the plant (for example an isolated and/or purified peptide, a synthetic peptide or a recombinant peptide), or a peptide produced in the plant following the non-natural introduction of a nucleic acid encoding for said miPEP in said plant.

The plant in which the miPEP has not been introduced has a basal quantity of said miPEP, which corresponds to that of said miPEP that is present naturally. The use of a miPEP comprising, or consisting of, a sequence identical to that of said miPEP leads to an increase in the total quantity of miPEP, which modulates the accumulation of the miRNA the primary transcript of which contains the sequence encoding for said miPEP.

Moreover, the miPEP introduced is present in the plant and its introduction does not affect its stability.

In the invention, by "accumulation" is meant the production of a molecule, such as a miRNA or a miPEP, in the cell.

Thus, "modulation of the accumulation" of a molecule in a cell corresponds to a change in the quantity of this molecule in the cell.

In an embodiment, the invention relates to the use as defined above, in which the modulation of the accumulation of said miRNA is a decrease or an increase in the accumulation of said miRNA, in particular an increase A "decrease in the accumulation of miRNA" corresponds to a lowering of the quantity of said molecule in the cell.

Conversely, an "increase in the accumulation of miRNA" corresponds to an increase in the quantity of said molecule in the cell.

In an embodiment, the invention relates to the use as defined above in which said gene involved in the mycorrhizal symbiosis encodes a transcription factor of the GRAS family.

In an embodiment, the invention relates to the use as defined above, in which said gene, involved in the mycorrhizal symbiosis, is selected from the group consisting of: HAM1 (Accession n° MTGI9-TC114268) and HAM2 (Accession n° MTGI9-TC120850) (accession numbers according to the *Medicago truncatula* Gene Expression Atlas "MtGEA") data bank.

In an embodiment, the invention relates to the use as defined above, in which said miRNA is miR171b, in particular, in which miR171b has a nucleotide sequence consisting of SEQ ID NO: 1.

In particular, the invention relates to the use as defined above, in which said miR171b has a nucleotide sequence having at least 80% identity, preferably at least 90% identity, with the nucleotide sequence SEQ ID NO: 1.

In an embodiment, the invention relates to the use as defined above, in which said miPEP is miPEP171b, in particular, in which said miPEP171b has an amino acid sequence consisting of SEQ ID NO: 2.

In particular, the invention relates to the use as defined above, in which said miPEP171b has an amino acid sequence having at least 80% identity, preferably at least 90% identity, with the amino acid sequence SEQ ID NO: 2.

In an embodiment, the invention relates to the use as defined above, in which said miRNA is slmiR171e, in particular, in which said slmiR171e has a nucleotide sequence consisting of SEQ ID NO: 5.

In particular, the invention relates to the use as defined above, in which said slmiR171e has a nucleotide sequence having at least 80% identity, preferably at least 90% identity, with the nucleotide sequence SEQ ID NO: 5.

In an embodiment, the invention relates to the use as defined above, in which said miPEP is slmiPEP171e, in particular, in which said slPEP171e has an amino acid sequence consisting of SEQ ID NO: 6.

In particular, the invention relates to the use as defined above, in which said slmiPEP171e has amino acids having at least 80% identity, preferably at least 90% identity, with the amino acid sequence SEQ ID NO: 6.

In an embodiment, the invention relates to the use as defined above, in which said miRNA is ljmiR171b, in particular, in which said ljmiR171b has a nucleotide sequence consisting of SEQ ID NO: 9.

In particular, the invention relates to the use as defined above, in which said ljmiR171b has a nucleotide sequence having at least 80% identity, preferably at least 90% identity, with the nucleotide sequence SEQ ID NO: 9.

In an embodiment, the invention relates to the use as defined above, in which said miPEP is ljmiPEP171b, in particular, in which said ljPEP171b has an amino acid sequence consisting of SEQ ID NO: 10.

In particular, the invention relates to the use as defined above, in which said ljmiPEP171b has amino acids having at least 80% identity, preferably at least 90% identity, with the amino acid sequence SEQ ID NO: 10.

In an embodiment, the invention relates to the use as defined above, in which said miRNA is osmiR171i, in particular, in which said osmiR171i has a nucleotide sequence consisting of SEQ ID NO: 13.

In particular, the invention relates to the use as defined above, in which said osmiR171i has a nucleotide sequence having at least 80% identity, preferably at least 90% identity, with the nucleotide sequence SEQ ID NO: 13.

In an embodiment, the invention relates to the use as defined above, in which said miPEP is osmiPEP171i, in particular, in which said osmiPEP171i has an amino acid sequence consisting of SEQ ID NO: 14.

In particular, the invention relates to the use as defined above, in which said osmiPEP171i has an amino acid sequence having at least 80% identity, preferably at least 90% identity, with the amino acid sequence SEQ ID NO: 14.

In an embodiment, the invention relates to the use as defined above, in which said plant is a monocotyledon plant such as *Oryza sativa* (rice), a dicotyledon plant, a leguminous plant such as *Glycine max* (soya), *Medicago truncatula* and *Medicago sativa* (alfalfa) or a solanaceous plant such as *Nicotiana benthamiana* (tobacco), *Solanum tuberosum* (potato), *Solanum lycopersicum* (tomato) or *Solanum melongena* (aubergine).

In an embodiment, the invention relates to the use as defined above, in which said plant is *Medicago truncatula, Medicago sativa* (alfalfa), *Solanum lycopersicum* (tomato), *Lotus japonicus* (birdsfoot trefoil) or *Oryza sativa* (rice).

In an embodiment, the invention relates to the use as defined above, in which said plant is selected from *Medicago truncatula, M. sativa* and *Glycine max* (soya).

In an embodiment, the invention relates to the use as defined above, in which said plant is *Medicago truncatula*.

In an embodiment, the invention relates to the use as defined above, in which said fungus is an endomycorrhizal or ectomycorrhizal fungus, preferably endomycorrhizal.

In an embodiment, the invention relates to the use as defined above, in which said fungus is a glomeromycete or basidiomycete or ascomycete fungus, preferably glomeromycete.

Non-limitatively, a mycorrhizal fungus can for example be selected from the list indicated below:
ectomycorrhizal fungi:
*Tuber* sp.
*Boletus* sp.
*Lactarius* sp.
*Cantharellus* sp.
endomycorrhizal fungi (glomeromycetes):
*Glomus* sp.
*Rhizophagus* sp.
*Gigaspora* sp.

*Acaulospora* sp.

*Scutellospora* sp.

In an embodiment, the invention relates to the use as defined above, in which said fungus is a glomeromycete.

In an embodiment, said fungus is *Rhizophagus irregularis*.

In an embodiment, the invention relates to the use as defined above, for promoting the arbuscular mycorrhizal symbiosis between a *Medicago truncatula* plant and a glomeromycete fungus, in which the miPEP171b is introduced exogenously into said *M. truncatula* plant, said miPEP171b also being naturally present in said *M. truncatula* plant, said miPEP171b introduced exogenously being a peptide the sequence of which comprises or consists of a sequence identical to that of said miPEP171b naturally present, said sequence of the miPEP171b naturally present being encoded by an open reading frame situated at 5' on the primary transcript of the miR171b, which miR171b regulates the expression of at least one gene involved in the mycorrhizal symbiosis in *M. truncatula*, the sum of the quantity of said miPEP171b introduced exogenously and that of said miPEP171b naturally present being strictly greater than the quantity of said miPEP171b naturally present in said *Medicago truncatula* plant.

In an embodiment, the invention relates to the use as defined above, for promoting the arbuscular mycorrhizal symbiosis between a *Solanum lycopersicum* plant and a glomeromycete fungus, in which the slmiPEP171e is introduced exogenously into said *Solanum lycopersicum* plant, said slmiPEP171e also being naturally present in said *Solanum lycopersicum* plant, said slmiPEP171e introduced exogenously being a peptide the sequence of which comprises or consists of a sequence identical to that of said slmiPEP171e naturally present, said sequence of the slmiPEP171e naturally present being encoded by an open reading frame situated at 5' on the primary transcript of the slmiR171e, said slmiR171e regulating the expression of at least one gene involved in the mycorrhizal symbiosis in *Solanum lycopersicum*, the sum of the quantity of said slmiPEP171e introduced exogenously and that of said slmiPEP171e naturally present being strictly greater than the quantity of said slmiPEP171e naturally present in said *Solanum lycopersicum* plant.

In an embodiment, the invention relates to the use as defined above, for promoting the arbuscular mycorrhizal symbiosis between a *Lotus japonicus* plant and a glomeromycete fungus, in which the ljmiPEP171b is introduced exogenously into said plant *Lotus japonicus*, said ljmiPEP171b also being naturally present in said *Lotus japonicus* plant, said ljmiPEP171b introduced exogenously being a peptide the sequence of which comprises or consists of a sequence identical to that of said ljmiPEP171b naturally present, said sequence of the ljmiPEP171b naturally present being encoded by an open reading frame situated at 5' on the primary transcript of the ljmiR171b, said ljmiR171b regulating the expression of at least one gene involved in the mycorrhizal symbiosis in *Lotus japonicus*, the sum of the quantity of said ljmiPEP171b introduced exogenously and that of said ljmiPEP171b naturally present being strictly greater than the quantity of said ljmiPEP171b naturally present in said *Lotus japonicus* plant.

In an embodiment, the invention relates to the use as defined above, for promoting the arbuscular mycorrhizal symbiosis between an *Oryza sativa* plant and a glomeromycete fungus, in which the osmiPEP171i is introduced exogenously into said *Oryza sativa* plant, said osmiPEP171i also being naturally present in said *Oryza sativa* plant, said osmiPEP171i introduced exogenously being a peptide the sequence of which comprises or consists of a sequence identical to that of said naturally present osmiPEP171i, said sequence of the osmiPEP171i naturally present being encoded by an open reading frame situated at 5' on the primary transcript of the osmiR171i, said miR171i regulating the expression of at least one gene involved in the mycorrhizal symbiosis in *Oryza sativa*, the sum of the quantity of said osmiPEP171i introduced exogenously and that of said osmiPEP171i naturally present being strictly greater than the quantity of said osmiPEP171i naturally present in said plant *Oryza sativa*.

In an embodiment, the invention relates to the use as defined above, in which said miPEP is introduced into the plant externally, preferably by watering, spraying, or by adding a fertilizer, compost, a culture substrate or a support in contact with the plant.

In an embodiment, the invention relates to the use as defined above, in which said miPEP is introduced externally into a grain or a seed, preferably by watering, by spraying or by adding a fertilizer, a compost, a culture substrate or a support in contact with the grain or the seed.

In an embodiment, the invention relates to the use as defined above, in which said miPEP is introduced by watering, in particular by spraying.

In an embodiment, the invention relates to the use as defined above, in which said miPEP is introduced by watering and by adding a fertilizer.

In an embodiment, the invention relates to the use as defined above, in which said miPEP is introduced by adding a fertilizer.

In an embodiment, the invention relates to the use as defined above, in which said miPEP is introduced by watering, and by adding a fertilizer.

The inventors in fact found, unexpectedly, that it is possible to apply a composition comprising a miPEP directly onto the plant for modulating the accumulation of the corresponding miRNA in the plant, which indicates that the miPEP is taken up by the plant.

In an embodiment, the invention relates to the use as defined above, in which the plant is treated with a composition comprising $10^{-9}$ M to $10^{-4}$ M of said miPEP, in particular $10^{-9}$ M, $10^{-8}$ M, $10^{-7}$ M, $10^{-6}$ M, $10^{-5}$ M or $10^{-4}$ M of said miPEP.

Preferably, the compositions have a concentration from $10^{-8}$ M to $10^{-5}$ M for application by watering or by spraying on the plant.

In a complementary manner, more or less concentrated compositions can be envisaged for treating the plant with miPEP. For example, non limitatively, more concentrated compositions comprising $10^{-1}$ M to $10^{-3}$ M, in particular $10^{-2}$ M of miPEP, can be used in the case when the miPEP introduced exogenously is administered to the plant by spreading fertilizer.

The solubility properties of the miPEPs are determined in particular by their amino acid composition. The hydrophilic miPEPs can be solubilized and conditioned in aqueous solutions, such as water. The hydrophobic miPEPs can be solubilized and conditioned in solvents, such as organic solvents.

For treating plants with miPEPs, the organic solvents are solvents that are non-toxic for the plants in small quantities, i.e. they do not have harmful effects on the development of the plant. Non limitatively, the organic solvents can be selected from acetonitrile and acetic acid.

The miPEPs can also be solubilized and conditioned in mixtures of organic solvents, for example a mixture of acetonitrile and acetic acid. In particular, the miPEPs can be solubilized in a solution comprising 50% acetonitrile, 10% acetic acid and 40% water (volume/volume/volume).

In particular, the miPEP171b is solubilized in a solution comprising 50% acetonitrile, 10% acetic acid and 40% water (volume/volume/volume).

In particular, the miPEP171b solubilized in a solution comprising 50% acetonitrile, 10% acetic acid and 40% water (volume/volume/volume) is diluted to a concentration of $10^{-9}$M to $10^{-4}$ M with water.

In particular, the slmiPEP171e is solubilized in a solution comprising 50% acetonitrile and 50% water (volume/volume).

In particular, the slmiPEP171e solubilized in a solution comprising 50% acetonitrile and 50% water (volume/volume) is diluted to a concentration of $10^{-9}$M to $10^{-4}$ M with water.

In particular, the ljmiPEP171b is solubilized in water.

In particular, the ljmiPEP171b is at a concentration of $10^{-9}$ M to $10^{-4}$ M in water.

In particular, the osmiPEP171i is solubilized in a solution comprising 50% acetonitrile and 50% water (volume/volume).

In particular, the osmiPEP171i solubilized in a solution comprising 50% acetonitrile and 50% water (volume/volume) is diluted to a concentration of $10^{-9}$M to $10^{-4}$ M with water.

In an embodiment, the invention relates to the use as defined above, in which said miPEP is introduced into the plant by means of a nucleic acid encoding for said miPEP, said nucleic acid being introduced into the plant.

In an embodiment, the invention relates to the use as defined above, in which the percentage colonization by said fungus is increased in the plant into which said miPEP has been introduced relative to the percentage colonization by said fungus of an identical and plant of the same age into which a miPEP has not been introduced, or relative to the percentage colonization by said fungus of an identical plant of the same age in which said miPEP has not been introduced.

In an embodiment, the invention relates to the use as defined above, in which the number of arbuscules in the root zones is increased in the plant into which said miPEP has been introduced relative to the number of arbuscules in the root zones of an identical and plant of the same age into which a miPEP has not been introduced, or relative to the number of arbuscules in the root zones of an identical and plant of the same age in which said miPEP has not been introduced.

In an embodiment, the invention relates to the use as defined above, in which the surface area of the arbuscules is increased in the plant into which said miPEP has been introduced relative to the surface area of the arbuscules of an identical and plant of the same age into which a miPEP has not been introduced, or relative to the surface area of the arbuscules of an identical and plant of the same age in which said miPEP has not been introduced.

The increase of the parameters making it possible to determine and quantify the mycorrhizal symbiosis in the plant into which the miPEP was introduced (such as the percentage colonization, the number of arbuscules or also the surface area of the arbuscules) is preferably demonstrated by comparison with an identical plant (i.e. a plant of the same species and/or variety), of the same age and grown under the same conditions but into which a miPEP has not been introduced.

The invention also relates to the use of a miPEP introduced exogenously into a plant for promoting the mycorrhizal symbiosis between said plant and a fungus, said miPEP being encoded by the primary transcript, introduced into the plant artificially, of a miRNA, said primary transcript, said miRNA and said miPEP not being naturally present in the plant, said miPEP being capable of modulating the accumulation of said miRNA in said plant, which miRNA regulates the expression of at least one gene involved in the mycorrhizal symbiosis in said plant.

In a particular embodiment, said primary transcript of the miRNA, the miRNA and said miPEP are introduced into the plant by means of a vector.

In another aspect, the invention relates to a method for promoting the mycorrhizal symbiosis between a plant and a fungus, and in particular the arbuscular mycorrhizal symbiosis (AM), comprising a step of introducing a miPEP into a plant exogenously, said miPEP also being naturally present in said plant, said miPEP introduced exogenously being a peptide of 3 to 100 amino acids, in particular of 4 to 100 amino acids, the sequence of which comprises or consists of a sequence identical to that of said miPEP naturally present, said sequence of the miPEP naturally present being encoded by an open reading frame situated at 5' on the primary transcript of a miRNA, said miPEP being capable of modulating the accumulation of said miRNA, which miRNA regulates the expression of at least one gene involved in the mycorrhizal symbiosis in said plant, of the quantity of said miPEP introduced exogenously and that of said miPEP naturally present being strictly greater than the quantity of said miPEP naturally present.

In an embodiment, the invention relates to a method as defined above in which said gene involved in the mycorrhizal symbiosis encodes a transcription factor of the GRAS family.

In an embodiment, the invention relates to a method as defined above, in which said gene, involved in the mycorrhizal symbiosis, is selected from the group consisting of: HAM1 (Accession n° MTGI9-TC114268) and HAM2 (Accession n° MTGI9-TC120850).

In an embodiment, the invention relates to a method as defined above, in which said miRNA is miR171b, in particular, in which said miR171b has a nucleotide sequence consisting of SEQ ID NO: 1.

In an embodiment, the invention relates to a method as defined above, in which said miPEP is miPEP171b, in particular, in which said miPEP171b has an amino acid sequence consisting of SEQ ID NO: 2.

In an embodiment, the invention relates to a method as defined above, in which said miRNA is slmiR171e, in particular, in which said slmiR171e has a nucleotide sequence consisting of SEQ ID NO: 5.

In an embodiment, the invention relates to a method as defined above, in which said miPEP is slmiPEP171e, in particular, in which said slmiPEP171e has an amino acid sequence consisting of SEQ ID NO: 6.

In an embodiment, the invention relates to a method as defined above, in which said miRNA is ljmiR171b, in particular, in which said ljmiR171b has a nucleotide sequence consisting of SEQ ID NO: 9.

In an embodiment, the invention relates to a method as defined above, in which said miPEP is ljmiPEP171b, in particular, in which said ljmiPEP171b has an amino acid sequence consisting of SEQ ID NO: 10.

In an embodiment, the invention relates to a method as defined above, in which said miRNA is osmiR171i, in particular, in which said osmiR171i has a nucleotide sequence consisting of SEQ ID NO: 13.

In an embodiment, the invention relates to a method as defined above, in which said miPEP is osmiPEP171i, in particular, in which said osmiPEP171i has an amino acid sequence consisting of SEQ ID NO: 14.

In an embodiment, the invention relates to a method as defined above, in which said plant is a monocotyledon plant such as *Oryza sativa* (rice), a dicotyledon plant, a leguminous plant such as *Glycine max* (soya), *Medicago truncatula* and *Medicago sativa* (alfalfa) or a solanaceous plant such as *Nicotiana benthamiana* (tobacco), *Solanum tuberosum* (potato), *Solanum lycopersicum* (tomato) or *Solanum melongena* (aubergine).

In an embodiment, the invention relates to a method as defined above, in which said plant is *Medicago truncatula*, *Medicago sativa* (alfalfa), *Solanum lycopersicum* (tomato), *Lotus japonicus* (birdsfoot trefoil) or *Oryza sativa* (rice).

In an embodiment, the invention relates to a method as defined above, in which said plant is selected from *Medicago truncatula*, *M. sativa* and *Glycine Max* (soya).

In an embodiment, the invention relates to a method as defined above, in which said plant is *Medicago truncatula*.

In an embodiment, the invention relates to a method as defined above, in which said plant is *Solanum lycopersicum*.

In an embodiment, the invention relates to a method as defined above, in which said plant is *Lotus japonicus*.

In an embodiment, the invention relates to a method as defined above, in which said plant is *Oryza sativa*.

In an embodiment, the invention relates to a method as defined above, in which said fungus is an endomycorrhizal or ectomycorrhizal fungus, preferably endomycorrhizal.

In an embodiment, the invention relates to a method as defined above, in which said fungus is a glomeromycete or basidiomycete or ascomycete fungus, preferably glomeromycete.

In an embodiment, said fungus is *Rhizophagus irregularis*.

In an embodiment, the invention relates to a method as defined above, for promoting the arbuscular mycorrhizal symbiosis between a plant *Medicago truncatula* and a glomeromycete fungus, in which the miPEP171b is introduced exogenously into said plant *M. truncatula*, said miPEP171b also being naturally present in said *M. truncatula* plant, said miPEP171b introduced exogenously being a peptide comprising or consisting of a sequence identical to that of said miPEP171b naturally present, said miPEP171b naturally present being a peptide of 3 to 100 amino acids, in particular of 4 to 100 amino acids the sequence of which is encoded by an open reading frame situated at 5' on the primary transcript of the miR171b, said miPEP171b being capable of increasing the accumulation of said miR171b, said miR171b regulating the expression of at least one gene involved in mycorrhizal symbiosis in *M. truncatula*, the sum of the quantity of said miPEP171b introduced exogenously and that of said miPEP171b naturally present being strictly greater than the quantity of said miPEP171b naturally present.

In an embodiment, the invention relates to a method as defined above, for promoting the arbuscular mycorrhizal symbiosis between a *Solanum lycopersicum* plant and a glomeromycete fungus, in which the slmiPEP171e is introduced exogenously into said *Solanum lycopersicum* plant, said slmiPEP171e also being naturally present in said *Solanum lycopersicum* plant, said slmiPEP171e introduced exogenously being a peptide comprising or consisting of a sequence identical to that of said slmiPEP171e naturally present, said slmiPEP171e naturally present being a peptide of 3 to 100 amino acids, in particular of 4 to 100 amino acids, the sequence of which is encoded by an open reading frame situated at 5' on the primary transcript of the slmiR171e, said slmiPEP171e being capable of increasing the accumulation of said slmiR171e, said slmiR171e regulating the expression of at least one gene involved in mycorrhizal symbiosis in *Solanum lycopersicum*, the sum of the quantity of said slmiPEP171e introduced exogenously and that of said slmiPEP171e naturally present being strictly greater than the quantity of said slmiPEP171e naturally present.

In an embodiment, the invention relates to a method as defined above, for promoting the arbuscular mycorrhizal symbiosis between a *Lotus japonicus* plant and a glomeromycete fungus, in which the ljmiPEP171b is introduced exogenously into said *Lotus japonicus* plant, said ljmiPEP171b also being naturally present in said *Lotus japonicus* plant, said ljmiPEP171b introduced exogenously being a peptide comprising or consisting of a sequence identical to that of said ljmiPEP171b naturally present, said ljmiPEP171b naturally present being a peptide of 3 to 100 amino acids, in particular of 4 to 100 amino acids, the sequence of which is encoded by an open reading frame situated at 5' on the primary transcript of the ljmiR171b, said ljmiPEP171b being capable of increasing the accumulation of said ljmiR171b, said ljmiR171b regulating the expression of at least one gene involved in mycorrhizal symbiosis in *Lotus japonicus*, the sum of the quantity of said ljmiPEP171b introduced exogenously and that of said ljmiPEP171b naturally present being strictly greater than the quantity of said ljmiPEP171b naturally present.

In an embodiment, the invention relates to a method as defined above, for promoting the arbuscular mycorrhizal symbiosis between an *Oricea sativa* plant and a glomeromycete fungus, in which the osmiPEP171i is introduced exogenously in said *Oricea sativa* plant, said osmiPEP171i also being naturally present in said *Oricea sativa* plant, said osmiPEP171i introduced exogenously being a peptide comprising or consisting of a sequence identical to that of said osmiPEP171i naturally present, said osmiPEP171i naturally present being a peptide of 3 to 100 amino acids, in particular of 4 to 100 amino acids, the sequence of which is encoded by an open reading frame situated at 5' on the primary transcript of the osmiR171i, said osmiPEP171i being capable of increasing the accumulation of said osmiR171i, said osmiR171i regulating the expression of at least one gene involved in the mycorrhizal symbiosis in *Oricea sativa*, the sum of the quantity of said osmiPEP171i introduced exogenously and that of said osmiPEP171i naturally present being strictly greater than the quantity of said osmiPEP171i naturally present.

In an embodiment, the invention relates to a method as defined above, in which said miPEP is introduced externally into the plant, preferably by watering, by spraying or by adding a fertilizer, a compost, a culture substrate or a support in contact with the plant.

In an embodiment, the invention relates to a method as defined above, in which said miPEP is introduced externally into a grain or a seed, preferably by watering, by spraying or by adding a fertilizer, a compost, a culture substrate or a support in contact with the grain or the seed.

In an embodiment, the invention relates to a method as defined above, in which said miPEP is administered to the plant in the form of a composition comprising $10^{-9}$ M to $10^{-4}$ M of said miPEP, in particular $10^{-9}$, $10^{-8}$, $10^{-7}$, $10^{-6}$, $10^{-5}$ or $10^{-4}$ M of said miPEP.

In an embodiment, the invention relates to a method as defined above, in which said miPEP is introduced into the plant by means of a nucleic acid encoding said miPEP, said nucleic acid being introduced into the plant.

In an embodiment, the invention relates to a method as defined above, in which the percentage colonization by said fungus is increased in the plant into which said miPEP has been introduced relative to the percentage colonization by said fungus of an identical and plant of the same age into which a miPEP has not been introduced, or relative to the percentage colonization by said fungus of an identical and plant of the same age in which said miPEP has not been introduced.

In an embodiment, the invention relates to a method as defined above, in which the number of arbuscules in the root zones is increased in the plant in which said miPEP has been introduced relative to the number of arbuscules in the root zones of an identical and plant of the same age into which a miPEP has not been introduced, or relative to the number of arbuscules in the root zones of an identical and plant of the same age in which said miPEP has not been introduced.

In an embodiment, the invention relates to a method as defined above, in which the surface area of the arbuscules is increased in the plant in which said miPEP has been introduced relative to the surface area of the arbuscules of an identical and plant of the same age into which a miPEP has not been introduced, or relative to the surface area of the arbuscules of an identical and plant of the same age in which said miPEP has not been introduced.

In another aspect, the invention relates to a plant in which a miPEP was introduced according to the use or the method for promoting the mycorrhizal symbiosis described above.

In another aspect, the invention relates to a method for the production of a transgenic plant comprising:
a) a step of introducing a nucleic acid encoding for a miPEP of 3 to 100 amino acids, in particular of 4 to 100 amino acids in a plant, or in at least one cell of said plant, under conditions allowing the expression of said miPEP,
said miPEP also being naturally present in said plant, said miPEP naturally present is a peptide the sequence of which is encoded by an open reading frame situated at 5' on the primary transcript of a miRNA, said miPEP being capable of modulating the accumulation of said miRNA in the plant, which miRNA regulates the expression of at least one gene involved in the mycorrhizal symbiosis, in particular the arbuscular mycorrhizal symbiosis, and
b) a step of growing the plant, or of at least one cell of said plant, obtained in step a) under conditions allowing a transgenic plant to be obtained.

In an embodiment, the invention relates to a method for the production of a transgenic plant as defined above, in which said transgenic plant obtained in step b) is more suitable for forming mycorrhizal symbiosis relative to an identical plant in which said nucleic acid has not been introduced.

In an embodiment, the invention relates to a method for the production of a transgenic plant as defined above, in which step a) is carried out using a vector containing said nucleic acid, preferably a plasmid.

In an embodiment, the invention relates to a method for the production of a transgenic plant as defined above, in which said nucleic acid does not comprise the complete sequence of said miRNA.

In an embodiment, the invention relates to a method for the production of a transgenic plant as defined above, in which the expression of said nucleic acid of step a) is placed under the control of a strong promoter, preferably a strong constitutive promoter such as the 35S promoter.

In an embodiment, the invention relates to a method for the production of a transgenic plant as defined above, in which said gene involved in the mycorrhizal symbiosis encodes a transcription factor of the GRAS family.

In an embodiment, the invention relates to a method for the production of a transgenic plant as defined above, in which said gene, involved in the development of the vegetative or reproductive parts of the plant, is selected from the group consisting of: HAM1 (Accession no MTGI9-TC114268) and HAM2 (Accession no MTGI9-TC120850).

In an embodiment, the invention relates to a method for the production of a transgenic plant as defined above, in which said miRNA is miR171b, in particular, in which said miR171b has a nucleotide sequence consisting of SEQ ID NO: 1.

In an embodiment, the invention relates to a method for the production of a transgenic plant as defined above, in which said miPEP is miPEP171b, in particular, in which said miPEP171b has an amino acid sequence consisting of SEQ ID NO: 2.

In an embodiment, the invention relates to a method for the production of a transgenic plant as defined above, in which said nucleic acid introduced in step a) comprises a nucleotide sequence consisting of SEQ ID NO: 3.

In an embodiment, the invention relates to a method for the production of a transgenic plant as defined above, in which said miRNA is slmiR171e, in particular, in which said slmiR171e has a nucleotide sequence consisting of SEQ ID NO: 5.

In an embodiment, the invention relates to a method for the production of a transgenic plant as defined above, in which said miPEP is slmiPEP171e, in particular, in which said slmiPEP171e has an amino acid sequence consisting of SEQ ID NO: 6.

In an embodiment, the invention relates to a method for the production of a transgenic plant as defined above, in which said nucleic acid introduced in step a) comprises a nucleotide sequence consisting of SEQ ID NO: 7.

In an embodiment, the invention relates to a method for the production of a transgenic plant as defined above, in which said miRNA is ljmiR171b, in particular, in which said ljmiR171b has a nucleotide sequence consisting of SEQ ID NO: 9.

In an embodiment, the invention relates to a method for the production of a transgenic plant as defined above, in which said miPEP is ljmiPEP171b, in particular, in which said ljmiPEP171b has an amino acid sequence consisting of SEQ ID NO: 10.

In an embodiment, the invention relates to a method for the production of a transgenic plant as defined above, in which said nucleic acid introduced in step a) comprises a nucleotide sequence consisting of SEQ ID NO: 11.

In an embodiment, the invention relates to a method for the production of a transgenic plant as defined above, in which said miRNA is osmiR171i, in particular, in which said osmiR171i has a nucleotide sequence consisting of SEQ ID NO: 13.

In an embodiment, the invention relates to a method for the production of a transgenic plant as defined above, in which said miPEP is osmiPEP171i, in particular, in which said osmiPEP171i has an amino acid sequence consisting of SEQ ID NO: 14.

In an embodiment, the invention relates to a method for the production of a transgenic plant as defined above, in which said nucleic acid introduced in step a) comprises a nucleotide sequence consisting of SEQ ID NO: 15.

In an embodiment, the invention relates to a method as defined above, in which said plant is a monocotyledon plant such as *Oryza sativa* (rice), a dicotyledon plant, a leguminous plant such as *Glycine max* (soya), *Medicago truncatula* and *Medicago sativa* (alfalfa) or a solanaceous plant such as *Nicotiana benthamiana* (tobacco), *Solanum tuberosum* (potato), *Solanum lycopersicum* (tomato) or *Solanum melongena* (aubergine).

In an embodiment, the invention relates to a method for the production of a transgenic plant as defined above, in which said plant is *Medicago truncatula, Medicago sativa* (alfalfa), *Solanum lycopersicum* (tomato), *Lotus japonicus* (birdsfoot trefoil) or *Oryza sativa* (rice).

In an embodiment, the invention relates to a method for the production of a transgenic plant as defined above, in which said plant is selected from *Medicago truncatula, M. sativa* and *Glycine max* (soya).

In an embodiment, the invention relates to a method for the production of a transgenic plant as defined above, in which said transgenic plant is *Medicago truncatula*.

In an embodiment, the invention relates to a method for the production of a transgenic plant as defined above, in which said transgenic plant is *Solanum lycopersicum*.

In an embodiment, the invention relates to a method for the production of a transgenic plant as defined above, in which said transgenic plant is *Lotus japonicus*.

In an embodiment, the invention relates to a method for the production of a transgenic plant as defined above, in which said transgenic plant is *Oryza sativa*.

In an embodiment, the invention relates to a method for the production of a transgenic plant as defined above, comprising:
a) a step of introducing a nucleic acid containing the nucleotide sequence SEQ ID NO: 3, encoding miPEP171b consisting of the amino acid sequence SEQ ID NO: 2, in a *M. truncatula* plant, or in at least one cell of said *M. truncatula* plant, under conditions allowing the expression of miPEP171b, said miPEP171b also being naturally present in said *M. truncatula* plant, said miPEP naturally present is a peptide the sequence of which is encoded by an open reading frame situated at 5' on the primary transcript of the miR171b, said miPEP171b being capable of modulating the accumulation of said miR171, said miR171b regulating the expression of at least one gene involved in the mycorrhizal symbiosis in *M. truncatula*, and
b) a step of growing the plant, or at least one cell of said plant, obtained in step a) under conditions allowing a transgenic *M. truncatula* plant to be obtained.

In an embodiment, the invention relates to a method for the production of a transgenic plant as defined above, comprising:
a) a step of introducing a nucleic acid containing the nucleotide sequence SEQ ID NO: 7, encoding slmiPEP171e consisting of the amino acid sequence SEQ ID NO: 6, in a *Solanum lycopersicum* plant, or in at least one cell of said *Solanum lycopersicum* plant, under conditions allowing the expression of slmiPEP171e, said slmiPEP171e also being naturally present in said *Solanum lycopersicum* plant, said slmiPEPe naturally present being a peptide the sequence of which is encoded by an open reading frame situated at 5' on the primary transcript of the slmiR171e, said slmiPEP171e being capable of modulating the accumulation of said slmiR171e, said slmiR171e regulating the expression of at least one gene involved in mycorrhizal symbiosis in *Solanum lycopersicum*, and
b) a step of growing the plant, or at least one cell of said plant, obtained in step a) under conditions allowing a transgenic *Solanum lycopersicum* plant to be obtained.

In an embodiment, the invention relates to a method for the production of a transgenic plant as defined above, comprising:
a) a step of introducing a nucleic acid containing the nucleotide sequence SEQ ID NO: 11, encoding ljmiPEP171b consisting of the amino acid sequence SEQ ID NO: 10, in a *Lotus japonicus* plant, or in at least one cell of said *Lotus japonicus* plant under conditions allowing the expression of ljmiPEP171b, said ljmiPEP171b also being naturally present in said plant *Lotus japonicus*, said ljmiPEPb naturally present being a peptide the sequence of which is encoded by an open reading frame situated at 5' on the primary transcript of the ljmiR171b, said ljmiPEP171b being capable of modulating the accumulation of said ljmiR171b, said ljmiR171b regulating the expression of at least one gene involved in mycorrhizal symbiosis in *Lotus japonicus* and
b) a step of growing the plant, or at least one cell of said plant, obtained in step a) under conditions allowing a transgenic *Lotus japonicus* plant to be obtained.

In an embodiment, the invention relates to a method for the production of a transgenic plant as defined above, comprising:
a) a step of introducing a nucleic acid containing the nucleotide sequence SEQ ID NO: 15, encoding osmiPEP171i consisting of the amino acid sequence SEQ ID NO: 14, in an *Oricea sativa* plant, or in at least one cell of said *Oricea sativa* plant under conditions allowing the expression of osmiPEP171i, said osmiPEP171i also being naturally present in said plant *Oricea sativa*, said osmiPEPi naturally present being a peptide the sequence of which is encoded by an open reading frame situated at 5' on the primary transcript of the osmiR171i, said miPEP171i being capable of modulating the accumulation of said osmiR171i, said osmiR171i regulating the expression of at least one gene involved in the mycorrhizal symbiosis in *Oricea sativa*, and
b) a step of growing the plant, or at least one cell of said plant, obtained in step a) under conditions allowing a transgenic *Oricea sativa* plant to be obtained.

In an embodiment, the invention relates to a production method as defined above, in which said miPEP is introduced into the plant by means of a nucleic acid encoding said miPEP, said nucleic acid being introduced into the plant.

In an embodiment, the invention relates to a method for the production of a transgenic plant as defined above, in which the percentage colonization by said fungus is increased in the plant in which said miPEP has been introduced relative to the percentage colonization by said fungus of an identical and plant of the same age into which a miPEP has not been introduced, or relative to the percentage colonization by said fungus of an identical and plant of the same age in which said miPEP has not been introduced.

In an embodiment, the invention relates to a method for the production of a transgenic plant as defined above, in which the number of arbuscules in the root zones is increased in the plant in which said miPEP has been introduced relative to the number of arbuscules in the root zones of an identical and plant of the same age into which a miPEP has not been introduced, or relative to the number of arbuscules in the root zones of an identical and plant of the same age in which said miPEP has not been introduced.

In an embodiment, the invention relates to a method for the production of a transgenic plant as defined above, in which the surface area of the arbuscules is increased in the plant in which said miPEP has been introduced relative to the surface area of the arbuscules of an identical plant of the same age into which a miPEP has not been introduced, or relative to the surface area of the arbuscules of an identical and plant of the same age in which said miPEP has not been introduced.

In an aspect, the invention also relates to a transgenic plant as obtained by the production methods as defined above.

In another aspect, the invention relates to a composition, in particular a phytosanitary composition, comprising miPEP171b as the active ingredient, said miPEP171b preferably consisting of SEQ ID NO: 2.

In another aspect, the invention relates to a composition, in particular a phytosanitary composition, comprising slmiPEP171e as the active ingredient, said slmiPEP171e preferably consisting of SEQ ID NO: 6.

In another aspect, the invention relates to a composition, in particular a phytosanitary composition, comprising ljmiPEP171b as the active ingredient, said ljmiPEP171b preferably consisting of SEQ ID NO: 10.

In another aspect, the invention relates to a composition, in particular a phytosanitary composition, comprising osmiPEP171i as the active ingredient, said osmiPEP171i preferably consisting of SEQ ID NO: 14.

In another aspect, the invention relates to a composition as defined above, in which said miPEP171b is at a concentration of $10^{-9}$M to $10^{-4}$M, in particular $10^{-9}$, $10^{-8}$, $10^{-7}$, $10^{-6}$, $10^{-5}$ or $10^{-4}$ M.

Preferably, a composition as defined above has a concentration from $10^{-8}$ M to $10^{-5}$ M for application by watering or by spraying on the plant.

In a complementary manner, more or less concentrated compositions can be envisaged for treating the plant with the miPEP. For example, non limitatively, more concentrated compositions comprising $10^{-1}$ M to $10^{-3}$ M, in particular $10^{-2}$ M of the miPEP, can be used in the case when the miPEP introduced exogenously is administered to the plant by spreading fertilizer.

In another aspect, the invention relates to a composition as defined above, further comprising an excipient, a diluent or a solvent.

In an embodiment, the invention relates to a composition as defined above, formulated so as to form a coating.

In another aspect, the invention relates to a composition comprising, in combination, a quantity of seeds from a plant and a quantity of a peptide the sequence of which comprises or consists of a sequence identical to that of a miPEP naturally present in said plant.

In an embodiment, the invention relates to a composition comprising in combination a quantity of seeds of a plant, in particular *M. truncatula*, and a quantity of a peptide the sequence of which comprises or consists of a sequence identical to that of miPEP171b.

In an embodiment, the invention relates to a composition comprising in combination a quantity of seeds of a plant, in particular *Solanum lycopersicum*, and a quantity of a peptide the sequence of which comprises or consists of a sequence identical to that of slmiPEP171e.

In an embodiment, the invention relates to a composition comprising in combination a quantity of seeds of a plant, in particular *Lotus japonicus*, and a quantity of a peptide the sequence of which comprises or consists of a sequence identical to that of ljmiPEP171b.

In an embodiment, the invention relates to a composition comprising in combination a quantity of seeds of a plant, in particular *Oricea sativa*, and a quantity of a peptide the sequence of which comprises or consists of a sequence identical to that of osmiPEP171i.

In another aspect, the invention relates to a composition as defined above, further comprising an excipient, a diluent or a solvent.

In an embodiment, the invention relates to a composition as defined above, formulated so as to form a coated seed.

Coating can be carried out by the methods used conventionally in the agri-food industry and can be obtained using a material capable of disintegrating in a solvent or in soil, such as a binder or clay.

According to the invention, coating can be used for example for imparting particular properties to a miPEP composition, or to a composition of seeds in combination with a miPEP.

In another aspect, the invention relates to a protocol for the production of a recombinant peptide, the sequence of which comprises or consists of a sequence identical to that of a miPEP as defined above, comprising a step of transforming an organism with an expression vector encoding for said recombinant peptide.

In an embodiment, said organism is selected from the group comprising bacteria, yeasts, fungi (other than yeasts), animal cells, plants and animals.

In an embodiment, said organism is *Escherichia coli*.

In particular, the invention relates to a protocol for the production of a recombinant peptide as defined above, comprising the following steps:
  the nucleic acid encoding said recombinant peptide is bound to a nucleic acid encoding a tag, such as GST,
  the expression vector containing said nucleic acid encoding said recombinant peptide is introduced into the bacterium *E. coli*,
  the bacterium *E. coli* containing the expression vector is cultured in LB medium preferably up to an OD between 0.2 and 0.4,
  production of the recombinant peptide is induced with IPTG, preferably for 4 to 5 hours,
  the *E. coli* bacteria are centrifuged and lysed,
  the supernatant is filtered,
  said recombinant peptide is purified on a glutathione sepharose affinity column,
  if necessary, cleaving of GST with a protease.

In another aspect, the invention relates to an antibody specifically recognizing miPEP171b, in particular said miPEP171b consisting of SEQ ID NO: 2.

Such an antibody can be obtained by a method known to a person skilled in the art, such as for example by injecting said miPEP171b into a non-human animal in order to trigger an immunization reaction and the production of antibodies by said animal.

In another aspect, the invention relates to an antibody specifically recognizing slmiPEP171e, ljmiPEP171b or osmiPEP171i consisting respectively of SEQ ID NO: 5, SEQ ID NO: 9 and SEQ ID NO: 13.

In another aspect, the invention relates to a method for the immunolocalization of miPEP171b comprising a step of marking a biological sample of a plant with an antibody specifically recognizing said miPEP171b.

In another aspect, the invention relates to a method for the immunolocalization of slmiPEP171e comprising a step of marking a biological sample of a plant with an antibody specifically recognizing said slmiPEP171e.

In another aspect, the invention relates to a method for the immunolocalization of ljmiPEP171b comprising a step of marking a biological sample of a plant with an antibody specifically recognizing said ljmiPEP171b.

In another aspect, the invention relates to a method for the immunolocalization of osmiPEP171i comprising a step of marking a biological sample of a plant with an antibody specifically recognizing said osmiPEP171i.

In another aspect, the invention relates to a method for culturing mycorrhizal fungi, in particular arbuscular mycorrhizal fungi, comprising a step of placing said fungi in contact:
  with a mixture comprising a plant or a part of a plant, in particular a root culture, and a peptide the sequence of which comprises or consists of a sequence identical to that of a miPEP naturally present in said plant, said miPEP naturally present is a peptide the sequence of which is encoded by an open reading frame situated at 5' on the primary transcript of a miRNA, said miPEP being capable of modulating the accumulation of said miRNA, which miRNA regulates the expression of at least one gene involved in the mycorrhizal symbiosis in said plant, or
  with a transgenic plant as defined previously,
  the plant, the part of a plant, and the transgenic plant being suitable for forming a mycorrhizal symbiosis with said fungus.

In particular, the method of culturing mycorrhizal fungi as defined above is carried out under culture conditions allowing the growth, or even the improvement of the growth of the plant, the part of a plant, and the transgenic plant, and that of the fungus.

In particular, the method of culturing mycorrhizal fungi as defined above is carried out under culture conditions allowing mycorrhizal symbiosis between the fungus and the plant, the part of a plant or the transgenic plant.

In particular, the invention relates to a method of culturing mycorrhizal fungi as defined above, in which said fungus is a glomeromycete.

In an embodiment, the peptide present in the mixture is an isolated peptide, an isolated and/or purified peptide, a synthetic peptide or a recombinant peptide.

In an embodiment, the invention relates to a method of culturing mycorrhizal fungi as defined above, in which said miRNA is miR171b, in particular, in which said miR171b has a nucleotide sequence consisting of SEQ ID NO: 1.

In an embodiment, the invention relates to a method of culturing mycorrhizal fungi as defined above, in which said miPEP is miPEP171b, in particular, in which said miPEP171b has an amino acid sequence consisting of SEQ ID NO: 2.

In an embodiment, the invention relates to a method of culturing mycorrhizal fungi as defined above, in which said miRNA is slmiR171e, in particular, in which said slmiR171e has a nucleotide sequence consisting of SEQ ID NO: 5.

In an embodiment, the invention relates to a method of culturing mycorrhizal fungi as defined above, in which said miPEP is slmiPEP171e, in particular, in which said slmiPEP171e has an amino acid sequence consisting of SEQ ID NO: 6.

In an embodiment, the invention relates to a method of culturing mycorrhizal fungi as defined above, in which said miRNA is ljmiR171b, in particular, in which said ljmiR171b has a nucleotide sequence consisting of SEQ ID NO: 9.

In an embodiment, the invention relates to a method of culturing mycorrhizal fungi as defined above, in which said miPEP is ljmiPEP171b, in particular, in which said ljmiPEP171b has an amino acid sequence consisting of SEQ ID NO: 10.

In an embodiment, the invention relates to a method of culturing mycorrhizal fungi as defined above, in which said miRNA is osmiR171i, in particular, in which said osmiR171i has a nucleotide sequence consisting of SEQ ID NO: 13.

In an embodiment, the invention relates to a method of culturing mycorrhizal fungi as defined above, in which said miPEP is osmiPEP171i, in particular, in which said osmiPEP171i has an amino acid sequence consisting of SEQ ID NO: 14.

In particular, the invention relates to a method of culturing mycorrhizal fungi as defined above, in which part of a plant is a root or a fragment of roots.

In another aspect, the invention relates to a method for the production of spores of mycorrhizal fungi, in particular of the arbuscular mycorrhizal fungi, comprising a step of placing said fungi in contact:
  with a mixture comprising a plant, or a part of a plant, and a peptide the sequence of which comprises or consists of a sequence identical to that of a miPEP naturally present in said plant, said miPEP naturally present is a peptide the sequence of which is encoded by an open reading frame situated at 5' on the primary transcript of a miRNA, said miPEP being capable of modulating the accumulation of said miRNA, which miRNA regulates the expression of at least one gene involved in the mycorrhizal symbiosis in said plant, or
  with a transgenic plant as defined previously,
  the plant, the part of a plant, and the transgenic plant being suitable for forming a mycorrhizal symbiosis with said fungus.

In particular, the method of production of spores as defined above is carried out under culture conditions allowing the growth of the plant, the part of a plant, and the transgenic plant, and that of the fungus.

In particular, the method of production of spores as defined above is carried out under culture conditions allowing mycorrhizal symbiosis between the fungus and the plant, the part of a plant or the transgenic plant.

In particular, the invention relates to a method for the production of spores as defined above, in which said fungus is a glomeromycete.

In an embodiment, said fungus is *Rhizophagus irregularis*.

In an embodiment, the invention relates to a method for the production of spores as defined above, in which said miRNA is miR171b, in particular, in which said miR171b has a nucleotide sequence consisting of SEQ ID NO: 1.

In an embodiment, the invention relates to a method for the production of spores as defined above, in which said miPEP is miPEP171b, in particular, in which said miPEP171b has an amino acid sequence consisting of SEQ ID NO: 2.

In an embodiment, the invention relates to a method for the production of spores as defined above, in which said miRNA is slmiR171e in particular, in which said slmiR171e has a nucleotide sequence consisting of SEQ ID NO: 5.

In an embodiment, the invention relates to a method for the production of spores as defined above, in which said miPEP is slmiPEP171e, in particular, in which said slmiPEP171e has an amino acid sequence consisting of SEQ ID NO: 6.

In an embodiment, the invention relates to a method for the production of spores as defined above, in which said miRNA is the ljmiR171b, in particular, in which said ljmiR171b has a nucleotide sequence consisting of SEQ ID NO: 9.

In an embodiment, the invention relates to a method for the production of spores as defined above, in which said miPEP is ljmiPEP171b, in particular, in which said ljmiPEP171b has an amino acid sequence consisting of SEQ ID NO: 10.

In an embodiment, the invention relates to a method for the production of spores as defined above, in which said miRNA is osmiR171i, in particular, in which said osmiR171i has a nucleotide sequence consisting of SEQ ID NO: 13.

In an embodiment, the invention relates to a method for the production of spores as defined above, in which said miPEP is osmiPEP171i, in particular, in which said osmiPEP171i has an amino acid sequence consisting of SEQ ID NO: 14.

In particular, the invention relates to a method for the production of spores as defined above, in which said part of a plant is a root or a fragment of roots.

In another aspect, the invention relates to a method for producing inoculum of mycorrhizal fungi, in particular inoculum of arbuscular mycorrhizal fungi, comprising:
 a step of co-culturing fungi with a living plant material, called plant host, corresponding at least partially to a constitutive part of a plant root suitable for forming a symbiosis with said fungi, and
 a step of placing a quantity of a peptide in contact with the aforementioned co-culture, said peptide having a sequence comprising or consisting of a sequence identical to that of a miPEP naturally present in said plant host, said miPEP naturally present is a peptide the sequence of which is encoded by an open reading frame situated at 5' on the primary transcript of a miRNA, said miPEP being capable of modulating the accumulation of said miRNA, which miRNA regulates the expression of at least one gene involved in the mycorrhizal symbiosis in said plant host.

The invention also relates to a method for producing inoculum of mycorrhizal fungi, in particular inoculum of arbuscular mycorrhizal fungi, comprising a step of co-culture of fungi with a living plant material, called plant host, at least partially corresponding to a constitutive root part of a plant suitable for forming a symbiosis with said fungi, and said plant host being a transgenic plant or a plant in which a peptide has been introduced,
 said peptide having a sequence comprising or consisting of a sequence identical to that of a miPEP naturally present in said plant host, said miPEP naturally present is a peptide the sequence of which is encoded by an open reading frame situated at 5' on the primary transcript of a miRNA, said miPEP being capable of modulating the accumulation of said miRNA, which miRNA regulates the expression of at least one gene involved in the mycorrhizal symbiosis in said plant host.

The invention also relates to a method for producing inoculum of mycorrhizal fungi, in particular inoculum of arbuscular mycorrhizal fungi, comprising a mixing step containing:
 fungi,
 a living plant material, called plant host, corresponding at least partially, to a constitutive root part of a plant suitable for forming a symbiosis with said fungi, and
 a peptide,
 said peptide having a sequence comprising or consisting of a sequence identical to that of a miPEP naturally present in said plant host, said miPEP naturally present is a peptide the sequence of which is encoded by an open reading frame situated at 5' on the primary transcript of a miRNA, said miPEP being capable of modulating the accumulation of said miRNA, which miRNA regulates the expression of at least one gene involved in mycorrhizal symbiosis in said plant host.

In another aspect, the invention relates to an inoculum of mycorrhizal fungi, in particular an inoculum of arbuscular mycorrhizal fungi, suitable for the inoculation of a plant host, comprising at least one fungus and a peptide the sequence of which comprises or consists of a sequence identical to that of a miPEP naturally present in the plant host,
 said miPEP naturally present in the plant host being a peptide the sequence of which is encoded by an open reading frame situated at 5' on the primary transcript of a miRNA,
 said miPEP being capable of modulating the accumulation of said miRNA, which miRNA regulates the expression of at least one gene involved in the mycorrhizal symbiosis in said plant host.

Preferably, said miPEP is miPEP171b.

Said miPEP can also be selected from slmiPEP171e, ljmiPEP171b and osmiPEP171i.

The peptide used in order to produce inoculum, or the peptide present in the inoculum, is in particular an isolated peptide, an isolated and/or purified peptide, a synthetic peptide or a recombinant peptide.

Preferably, the inoculum also contains a plant or a part of a plant, in particular a root, a root culture or a part of a root.

In order to produce the inoculum, and in the inoculum, the fungus used can be in the form of spores or in the form of mycelium.

The sequences of the miPEP171b, its open reading frame, the miR171b and the primary transcripts of the miR171b in *M. truncatula* are shown in Table 1.

TABLE 1

| | | |
|---|---|---|
| miR171b | UGAUUGAGCCGCGUCAAUAUC | SEQ ID NO: 1 |
| miPEP171b | MLLHRLSKFCKIERDIVYIS | SEQ ID NO: 2 |
| miORF171b | ATGCTTCTTCATAGGCTCTCCAAATTTTGCAAAATTGAAAGAGGCATAGTATATATATCTTAG | SEQ ID NO: 3 |
| pri-miR171b | ATTGGTCAAACATACATACAGTAGCACTAGCTGGTTTCATTATTCCACTATGCTTCTTCATAGGCTCTCCAAATTTTGCAAAATTGAAAGAGGCATAGTATATATATCTTAGCAAGGAGAAATTCAGGATATTGAGGATGAAGATTGAAGAGTAATCAGTGATGAAGAAAGCAAGCAAGGTATTGGCGCGCCTCAATTTGAATACATGGCTATAAAAATGCATCATATCAGCCATGTAGTTTGATTGAACCGCGTCAATATCTTGTTTCCATCTCCAAATTTACCAATCTCATCAAATCAAAT | SEQ ID NO: 4 |

TABLE 1-continued

```
TAACACCACAATCAAGTCAAAATAGGTTGA
CCTTATCATCGAAGAAATTGTTTTCTCATTC
CTATCGAAGTTGGACTTGCTGAAAATGCTC
GAAAGCATGTGTTTTAGTTCGACAGGCGAA
AAAGTTACCGAAGGACAATTTGGTTGTGGT
TCGGATAAGGTCAAGCAACGGATATTTTCA
AGACACGTTCGAAATTCAAGTCAAATGGAT
AAGTATCGTTAGTTTACTGCAGTTATAGTTT
TAAATTCAAATCTAGGCAGTTATTTCTATTT
GTATAAATAGTAGTTTTTCCCTAGGGAAAA
AGGGTCGCAATTCAATCATACAAAAAACTT
ACAATCAAATTATCCGCATGGAAGAGAGAA
ACGAGTCACAAGTTGCAATGTATGAACATG
TGTACCAATTTACATTCAATCAGTACAATTT
T
```

The sequences of the slmiPEP171e, its open reading frame, the slmiR171e and the primary transcript of the slmiR171e in *Solanum lycopersicum* are shown in Table 2.

TABLE 2

| slmiR171e | uugagccgcgucaauaucucu | SEQ ID NO: 5 |
|---|---|---|
| slmiPEP171e | MKLGNIEGTYFIICLGRYI | SEQ ID NO: 6 |
| slmiORF171e | ATGAAGTTGGGAAATATTGAAGGTACGT ACTTTATAATATGTTTAGGAAGATATATA TAG | SEQ ID NO: 7 |
| slpri-miR171e | GTCTTTGAGGGCATGAATAGTGTAATAT GGACCCATTCGTGTGTGGAAAAATTGTA CAATATTCCAAGAAAAAACGTACCTGTC CACATTAATTAGTTAGGTAAGTGGATTAT ACTACTCATAAAATATTATATTACAGCCA AAGGAATCCAACTTCTCTAAAATAAAAA TAAAAAACACCAAATTAATGTTTGTTTCA ATATTTTGATGTACATTACTTTAGAGCAA GTATTAGCAAGATACATTAGGCTATTTTT TGTTTTTTCGGAATCACATCAAGAAATGA AAGATCTTTGGTCACAACATGATGAAGA TACATAGTTGAAACTTGAAAGATATAAT AGTTTTGATTTTTCGTATTGAAAATTATT CTGCAAATTGATGGATAGCTAGCTAATT CAAAGATGAAGTTGGGAAATATTGAAGG TACGTACTTTATAATATGTTTAGGAAGAT ATATATAGATATTGATGCGGTTCAATCTG AAAGACATGGTTAGATATGTAATTAGCC TTGTAATTTTGGATTGAGCCGCGTCAATA TCTCTCTTCCTATTTTCAATTAGTTTATAA GTAACTTGAACTTATTTAATTACTCGTT GGTAATACTTGTCTTGTTTCATGTTTTCCT CTTGGCCATGCATCTTTAATGTTTTTTTT CCACTAATTTTCTGGTTTTTAATTAGTTTT TAAATTTCTTCTTAATTTCATCTTTGACA CCATTAATTTCATTCGTTGCCGTTCGTTG ATAGACGTTTTGAATTAGATAGTTAATC ATAATTAATACATGAATGAATCGATCAA GAGCTAGCATGGAAATTAATGATTGTGT TGAATGATTTTTTTTGTATTATTTTTTGC TTCTTAAGGTAATTGCAACCTACTTTTGC TTATATATTTTCTTTTATTATTTGAATTTC GAGGTATTTTCACTACCTCAAATAATTAC CTTTCTTCCTGATTTCAATTTTCTTTCATA AAAAAGCGTCTTTCTAAA | SEQ ID NO: 8 |

The sequences of ljmiPEP171b, its open reading frame, the ljmiR171b and the primary transcript of the ljmiR171b in *Lotus japonicus* are shown in Table 3.

TABLE 3

| ljmiR171b | ugauugagccgcgucaauauc | SEQ ID NO: 9 |
|---|---|---|
| ljmiPEP171b | MYHRSKAKLCQTDGDDGGGSDM | SEQ ID NO: 10 |
| ljmiORF171b | ATGTATCATCGAAGCAAAGCAAAACTAT GTCAAACTGATGGTGATGATGGAGGAGG AAGTGATATGTGA | SEQ ID NO: 11 |
| ljpri-miR171b | GAGAAATACAAAAACCCAACAAAACCC AACTCAAAATATTATTCTCCACCAAGCA GAAACCAGATTTCATCTCGTTACAGTATC ACCATAGTCCACGCCCAACTCCAAAAGC CATGCCACAAGCCAAAACAAAACGTCAG GTACAGATCACAGGACAAAATAGCTTTT TTCCAATCAGCCCAAGTATACAAAGCAA AGATGATATAAAGTGGTCCATGATGGTG GGTGTAATTCGTATTAACAACTTAATTAA TATGTACATTAATGTACCATCTAACGGGT ATATGGAAATTCAGTCTCTTTCATGACCT TATATTTCGCCTCAATGCCTCATTATAGG CATCCATCCATGCAGATGAAATTCCAAT AACAACCTCCCCGTCTTAATTCAATTGAG ACAATATTTTGTTGGGATTTGCAAGGCAC TTAGAAAATAATTTTTGAAACACAAACA AAGCCACTTGATAGAGTCATAGAGGTAG TAGAACAGAAACACTTGGCGATTGAGTT TTGTTTTTTAAAGTATTTTTCGAAATTG AGGAGGAAAACTAATTAATATTTGCGCT CATTCGTGGGAAAAGTGGTCGTTGGTCA AAGAGTCGCACAAATATTATTTCAGCAC TTGTGGTTTGGTTTAATGGTTTTGATGAA TTCATTCCACTTTGCTTATTCCCCCAGTCT GCAACACAAAATGATGTGTTTTCCAAAA TTAAAGACAGATCTCAAAAGCAGGTGTT AGTTAATTTCCTCATGTATCATCGAAGCA AAGCAAAACTATGTCAAACTGATGGTGA TGATGGAGGAGGAAGTGATATGTGAAGC ACAAATTAACAAGGTATTGACGCGTCTC AATTTGAAGACATGGCTGGCTAACATGA AAACCAATCATGTAGTTTGATTGAGCCG CGTCAATATCTTGCTTTTGCGTACTTCTTT CCATGTCCATCTGGCCACCAATCTCAACT CAAACGCCCACCGGTATGTATAATCATT ATTGAATGCTTAATTGTGTTCTCTTAATT TTGTATAATCTATATTCATAGTACTGTTT CTCTTTCTGCAGAAAATCAAAATGCGTTA TACATCAGAAGTAGGTAAAATTGACGTA TCAGGTCAGCCATCACAGCTTGCACCAA TCATTATTATATTGTATTATCTGATATGC ACAAATTAATGGAAATTATAAAATCCTT TAAATGGTATAGTATAGGTGTGGAAA | SEQ ID NO: 12 |

The sequences of osmiPEP171i, its open reading frame, the osmiR171i and the primary transcript of the osmiR171i in *Oryza sativa* are shown in Table 4.

TABLE 4

| osmiR171i | ggauugagccgcgucaauauc | SEQ ID NO: 13 |
|---|---|---|
| osmiPEP171i | MIARYIEREMTSKLGRGRKRAARLVAVFL LG | SEQ ID NO: 14 |
| osmiORF171i | ATGATAGCTAGATATATCGAGAGGGAGA TGACCAGTAAGCTTGGAAGAGGAAGAAA GAGAGCTGCTAGGCTTGTTGCGGTCTTTT TGCTTGGGTAA | SEQ ID NO: 15 |
| ospri-miR171i | AGAAGAATGGTTGTGATTGATTGAGAGG AGGAGGTAGGTGAAGAAATAGCTTCATT TTAGGACAAGACACTGTGCTAAAAATAG CTATATTTTAGGACGGAGAGAGTAGATA AGCTAGTCCCGACCCCCCTCCTCTCCTCT CTTGCCCCGCCTATATAATCCCCAAACAT CGCTTTCTCTTGGAGTAGGAGAAGGGTA | SEQ ID NO: 16 |

TABLE 4-continued

```
GTAGTTTAAGCTATAGCTCTAAAGACAT
CACCATGCAACATTACTTGCGTTATTACT
ATACCTATCCACCACCTACACATTTTGTC
ATCTCCCTCTCTCTTTCTCTCTGATCTGTC
TCAGATGTTTATGCACATATACAAGTTAA
TAGTTCTGTGGATCTAGCAATCCCGGCTT
GTTTGTTTTTGCTGCTTTGGTTTGATGAT
AGCTAGATATATCGAGAGGGAGATGACC
AGTAAGCTTGGAAGAGGAAGAAAGAGA
GCTGCTAGGCTTGTTGCGGTCTTTTTGCT
TGGGTAAAAAGAGGTATTGGCGTGCCTC
AATCCGAAGGCATGGCTGATTACAGGCA
CCTCGACCGATCTAGCGCATGCAGCCAT
GTTTCTTGGATTGAGCCGCGTCAATATCT
CTCCTTGCTTCCTTACTTCATGTACTGTGT
CATGCTCAAGCATATGTCCCCTCTCCGAT
CTTCCTACCTCGTCGAGTTCGTCGGATCA
GTTCCCAAATTAAAGGTGTTATATATATA
TATATATATATATATATATATATATATAT
ATATATATATATATAGTAAATTTGTTTGG
TGCTCCATGGTGCCCGG
```

Pages 42 to 59 correspond to extracts from French Patent Application No. FR 13/60727 filed on 31 Oct. 2013 for "Micropeptides and their use for modulating gene expression"

Application FR 13 60727 relates to micropeptides (peptides encoded by microRNAs or "miPEPs") and use thereof for modulating gene expression.

microRNAs (miRNAs) are small non-encoding RNAs, of about 21 nucleotides after maturation, which control the expression of target genes at the post-transcriptional level, by degrading the target mRNA or by inhibiting translation thereof. The miRNAs are found in plants and animals.

The target genes are often key genes in developmental processes. They encode, for example, transcription factors or proteins of the proteasome.

Very little is known about the regulation of expression of miRNAs, but in particular it is known that the latter involves, like most encoding genes, an RNA polymerase II: this enzyme produces a primary transcript, called "pri-miRNA", which is then matured by a protein complex in particular containing the enzymes of the Dicer type. This maturation leads firstly to formation of a precursor of miRNA called "pre-miRNA", having a secondary structure in stem-and-loop form containing the miRNA and its complementary sequence miRNA*. Then the precursor is matured, which leads to formation of a shorter double-stranded RNA containing the miRNA and the miRNA*. The miRNA then comes under the control of the RISC complex, which cleaves the mRNA of the target gene or inhibits its translation.

Moreover, it has been shown that the presence of introns in the primary transcript of the microRNA increases expression of the mature microRNA (Schwab et al., EMBO Rep., 14(7): 615-21, 2013). However, owing to experimental difficulties, the primary transcripts of microRNAs, or pri-miRNAs, have received very little study.

About 50% of eukaryotic genes have, within their region 5'UTR (5' UnTranslated Region) upstream of the encoding sequence, small open reading frames. These small open reading frames (or "uORFs" for upstream ORFs) can play a role as regulator of translation, mainly in cis, by modulating the binding and the rate of the ribosomes on the mRNA, but also in trans according to a mechanism that is still unknown, by means of peptides encoded by said uORFs (Combier et al., Gene Dev, 22:1549-1559, 2008). By definition, the uORFS are present upstream of encoding genes.

Small ORFs have also recently been discovered in long non-encoding RNAs between genes (lincRNAs), the putative function of which, if any, is unknown (Ingolia et al., Cell, 147(4): 789-802, 2011; Guttman & Rinn, Nature, 482(7385): 339-46, 2012).

However, no example has yet been reported concerning the existence of ORFs encoding peptides within non-encoding microRNAs. Until now, microRNAs, and by extension their primary transcript, have always been regarded, owing to their particular mode of action, as non-encoding regulatory RNAs that do not produce any peptide.

One of the aspects of the subject-matter of application FR 13 60727 is to propose peptides capable of modulating the expression of microRNAs.

Another aspect of the subject-matter of application FR 13 60727 is to propose a means for modulating the expression of one or more target genes of a microRNA.

The subject-matter of application FR 13 60727 offers the advantage of allowing easier and more efficient control of the expression of genes targeted by the microRNAs, using a means other than microRNA.

The subject-matter of application FR 13 60727 thus relates to a method for detecting and identifying a micropeptide (miPEP) encoded by a nucleotide sequence contained in the sequence of the primary transcript of a microRNA, comprising:

a) a step of detecting an open reading frame of 15 to 303 nucleotides contained in the sequence of the primary transcript of said microRNA, then b) a step of comparison between:
the accumulation of said microRNA in a specified eukaryotic cell expressing said microRNA,
in the presence of a peptide encoded by a nucleotide sequence that is identical or degenerated relative to that of said open reading frame, said peptide being present in the cell independently of the transcription of the primary transcript of said microRNA, and
the accumulation of said microRNA in a eukaryotic cell of the same type as the aforesaid specified eukaryotic cell expressing said microRNA, in the absence of said peptide, in which a modulation of the accumulation of said microRNA in the presence of said peptide relative to the accumulation of said microRNA in the absence of said peptide indicates the existence of a micropeptide encoded by said open reading frame.

In a first step, the method for detecting and identifying a micropeptide therefore consists of detecting, on the primary transcript of a microRNA, the existence of an open reading frame potentially encoding a peptide.

The second step, in its turn, makes it possible to characterize said peptide, i.e. to determine whether said peptide corresponds to a peptide really produced in the cell, by searching for an effect of said peptide on the accumulation of said microRNA.

In order to detect an effect of the peptide on the accumulation of the microRNA, a large quantity of peptide is introduced into a first cell expressing said microRNA. The accumulation of the microRNA in this first cell is then measured and compared with the accumulation of the microRNA in a second cell identical to the first, but not containing said peptide.

Observation of a change in the quantities of microRNA between the cells in the presence and in the absence of the peptide thus indicates (i) that there is a peptide encoded on the primary transcript of said microRNA, (ii) that the sequence of this peptide is encoded by the open reading frame identified on the primary transcript of said microRNA, and (iii) that said peptide acts upon the accumulation of said microRNA.

The subject-matter of application FR 13 60727 is therefore based on the unexpected dual observation made by the inventors, that on the one hand there are open reading frames capable of encoding micropeptides present on the primary transcripts of microRNAs, and on the other hand that said micropeptides are capable of modulating the accumulation of said microRNAs.

In application FR 13 60727, the terms "microRNA", "non-encoding microRNA" and "miRNA" are equivalent and can be used interchangeably. They define small RNA molecules of about 21 nucleotides, which are not translated and do not lead to a peptide or a protein.

However, in this mature form, the microRNAs perform a function of regulation of certain genes by post-transcriptional mechanisms, for example via the RISC complex.

The primary transcript of the microRNA or "pri-miRNA" corresponds for its part to the RNA molecule directly obtained from transcription of the DNA molecule. Generally, this primary transcript undergoes one or more post-transcriptional modifications, which lead for example to a particular structure of the RNA or cleavage of certain parts of the RNA by splicing phenomena, and which lead to the precursor form of the microRNA or "pre-miRNA", then to the mature form of the microRNA or "miRNA".

The terms "micropeptides" and "miPEPs" (microRNA encoded PEPtides) are equivalent and can be used interchangeably. They define a peptide that is encoded by an open reading frame present on the primary transcript of a microRNA, and which is capable of modulating the accumulation of said microRNA. The micropeptides in the sense of application FR 13 60727 should not be understood as necessarily being peptides of small size, as "micro" does not correspond to the size of the peptide.

Taking into account the degeneration of the genetic code, one and the same micropeptide can be encoded by several nucleotide sequences. Such nucleotide sequences, differing from one another by at least one nucleotide but encoding one and the same peptide, are called "degenerated sequences".

The terms "open reading frame" or "ORF" are equivalent and can be used interchangeably. They correspond to a nucleotide sequence in a DNA or RNA molecule that can potentially encode a peptide or a protein: said open reading frame begins with a start codon, followed by a series of codons, and ends with a stop codon.

In application FR 13 60727, the ORFs can be called specifically "miORFs" when the latter are present on the primary transcripts of microRNA.

In application FR 13 60727, by "accumulation" is meant the production of a molecule, such as a microRNA or a micropeptide, in the cell.

Thus, "modulation" of the accumulation of a molecule in a cell corresponds to a change in the quantity of this molecule present in the cell.

In an embodiment, the subject-matter of application FR 13 60727 relates to a method for detecting and identifying a miPEP as defined above, in which the modulation of the accumulation of said microRNA is a decrease or an increase in the accumulation of said microRNA, in particular an increase.

A "decrease in the accumulation" corresponds to a lowering of the quantity of said molecule in the cell.

Conversely, an "increase in the accumulation" corresponds to an increase in the quantity of said molecule in the cell.

In an advantageous embodiment, the subject-matter of application FR 13 60727 relates to a method for detecting and identifying a miPEP as defined above, in which the modulation of the accumulation of said microRNA is an increase in the accumulation of said microRNA.

In an embodiment, the subject-matter of application FR 13 60727 relates to a method for detecting and identifying a miPEP as defined above, in which the presence of said peptide in the cell results from:
    the introduction of a nucleic acid encoding said peptide into the cell, or
    the introduction of said peptide into the cell In order to characterize a miPEP, it is necessary to have a cellular model expressing a microRNA, in which said peptide to be tested is present. For this, it is possible to introduce a peptide into the cell, either by bringing the cell into contact with said peptide, or by introducing a nucleic acid encoding said peptide into the cell, and said nucleic acid will then be translated into a peptide within the cell.

In an embodiment, the subject-matter of application FR 13 60727 relates to a method for detecting and identifying a miPEP as defined above, in which said open reading frame in step a) is contained in the 5' or 3' part of said primary transcript of the microRNA, preferably in the 5' part.

The 5' or 3' parts of the primary transcript of the microRNA correspond to the terminal parts of the RNA molecule, which are cleaved during maturation of the microRNA.

In an embodiment, the subject-matter of application FR 13 60727 relates to a method for detecting and identifying a miPEP as defined above, in which said microRNA is present in a wild-type plant cell.

In application FR 13 60727, a wild-type plant cell corresponds to a plant cell that has not been genetically modified by man.

In an embodiment, the subject-matter of application FR 13 60727 relates to a method for detecting and identifying a miPEP as defined above, in which said specified eukaryotic cell, and said eukaryotic cell of the same type as the aforesaid specified eukaryotic cell, used in step b, are plant cells, preferably cells of *Medicago truncatula* or of *Arabidopsis thaliana*.

In the method for detecting and identifying a micropeptide as defined above, after identifying an ORF capable of encoding a peptide on the primary transcript of a microRNA, it is necessary to have a cellular model possessing said microRNA and said peptide, so as to be able to demonstrate a possible effect of the peptide on said microRNA.

Two options are therefore conceivable:
    the cellular model in which the miORF has been identified and that in which the effect of the peptide on the miRNA is demonstrated are identical, or
    the cellular model in which the miORF has been identified and that in which the effect of the peptide on the miRNA is demonstrated are different.

In the first option, the cellular model used for observing an effect of the peptide is the same as that in which the primary transcript of said microRNA was isolated. In this cellular model, the specified eukaryotic cells contain said microRNA naturally and only the peptide to be tested has to be introduced into these cells. In this context, said microRNA is described as "of endogenous origin" as the latter exists naturally in the cells. Nevertheless, in a cell, other copies of a microRNA of endogenous origin can be added, for example by introducing a vector encoding said microRNA of endogenous origin into the cell.

In the second option, the cellular model used for observing an effect of the peptide is different from that in which the primary transcript of said microRNA was isolated. In this cellular model, the specified eukaryotic cells contain neither the microRNA, nor the peptide to be tested. These two elements must therefore be introduced into these cells. In this context, said microRNA is described as "of exogenous origin" as the latter does not exist naturally in the cells.

In an embodiment, the subject-matter of application FR 13 60727 relates to a method for detecting and identifying a miPEP as defined above, in which said microRNA is of endogenous origin in said eukaryotic cell and in said eukaryotic cell of the same type as the aforesaid specified eukaryotic cell, used in step b).

In an embodiment, the subject-matter of application FR 13 60727 relates to a method for detecting and identifying a miPEP as defined above in which said microRNA is of exogenous origin in said eukaryotic cell and in said eukaryotic cell of the same type as the aforesaid specified eukaryotic cell, used in step b), said eukaryotic cells containing a vector allowing the expression of said microRNA.

In an embodiment, the subject-matter of application FR 13 60727 relates to a method for detecting and identifying a miPEP as defined above, in which the accumulation of said microRNA is determined using quantitative RT-PCR or Northern blot.

In an embodiment, the subject-matter of application FR 13 60727 relates to a method for detecting and identifying a miPEP as defined above, in which the accumulation of said microRNA is determined using a DNA or RNA chip.

The accumulation of said microRNA can be determined using the techniques of molecular biology for assay of molecules of specific nucleic acids.

In another aspect, the subject-matter of application FR 13 60727 also relates to a method for detecting and identifying a microRNA the sequence of the primary transcript of which contains a nucleotide sequence encoding a miPEP, comprising:
  a) a step of detecting an open reading frame of 15 to 303 nucleotides contained in the sequence of the primary transcript of said microRNA, then
  b) a step of comparison between:
    the accumulation of said microRNA in a specified eukaryotic cell expressing said microRNA,
    in the presence of a peptide encoded by a nucleotide sequence that is identical or degenerated relative to that of said open reading frame, said peptide being present in the cell independently of the transcription of the primary transcript of said microRNA, and
    the accumulation of said microRNA in a eukaryotic cell, of the same type as the aforesaid specified eukaryotic cell expressing said microRNA, in the absence of said peptide,
  in which modulation of the accumulation of said microRNA in the presence of said peptide relative to the accumulation of said microRNA in the absence of said peptide indicates the existence of a microRNA the primary transcript of which contains a nucleotide sequence encoding a micropeptide.

In an embodiment, the subject-matter of application FR 13 60727 relates to a method for detecting and identifying a microRNA as defined above, in which the modulation of the accumulation of said microRNA is a decrease or an increase in the accumulation of said microRNA, in particular an increase.

In an embodiment, the subject-matter of application FR 13 60727 relates to a method for detecting and identifying a microRNA as defined above, in which the presence of said peptide in the cell results from:
  the introduction of a nucleic acid encoding said peptide into the cell, or
  the introduction of said peptide into the cell.

In an embodiment, the subject-matter of application FR 13 60727 relates to a method for detecting and identifying a microRNA as defined above, in which said open reading frame in step a) is contained in the 5' or 3' part of said primary transcript of the microRNA, preferably in the 5' part.

In an embodiment, the subject-matter of application FR 13 60727 relates to a method for detecting and identifying a microRNA as defined above, in which said microRNA is present in a wild-type plant cell.

In an embodiment, the subject-matter of application FR 13 60727 relates to a method for detecting and identifying a microRNA as defined above, in which said eukaryotic cell, and said eukaryotic cell of the same type as the aforesaid specified eukaryotic cell, used in step b) are plant cells, preferably cells of *Medicago truncatula*.

In an embodiment, the subject-matter of application FR 13 60727 relates to a method for detecting and identifying a microRNA as defined above, in which said microRNA is of endogenous origin in said eukaryotic cell and in said eukaryotic cell of the same type as the aforesaid specified eukaryotic cell, used in step b).

In an embodiment, the subject-matter of application FR 13 60727 relates to a method for detecting and identifying a microRNA as defined above in which said microRNA is of exogenous origin in said eukaryotic cell and in said eukaryotic cell of the same type as the aforesaid specified eukaryotic cell, used in step b), said eukaryotic cells containing a vector allowing the expression of said microRNA.

In an embodiment, the subject-matter of application FR 13 60727 relates to a method for detecting and identifying a microRNA as defined above, in which the accumulation of said microRNA is determined using quantitative RT-PCR or Northern blot.

In an embodiment, the subject-matter of application FR 13 60727 relates to a method for detecting and identifying a microRNA as defined above, in which the accumulation of said microRNA is determined using a DNA or RNA chip.

In another aspect, the subject-matter of application FR 13 60727 relates to a miPEP as obtained by applying the method as defined above.

In another aspect, the subject-matter of application FR 13 60727 also relates to a miPEP of 4 to 100 amino acids, preferably of 4 to 40 amino acids, encoded by a nucleotide sequence contained in the primary transcript of a microRNA, said miPEP being capable of modulating the accumulation of said microRNA in a eukaryotic cell.

Moreover, it should be noted that several miORFS can be identified on the primary transcript of a microRNA, indicating that a primary transcript of microRNA can potentially encode several miPEPs.

It should also be noted that the effect of a miPEP is generally specific for a single microRNA, namely that resulting from the primary transcript encoding said miPEP.

In an embodiment, the subject-matter of application FR 13 60727 relates to a miPEP as defined above, said nucleotide sequence being contained in the 5' or 3' part of said primary transcript of a microRNA, preferably in the 5' part.

In an embodiment, the subject-matter of application FR 13 60727 relates to a miPEP as defined above, said nucleotide sequence corresponding to the first open reading frame present on said primary transcript of a microRNA.

In an embodiment, the subject-matter of application FR 13 60727 relates to a miPEP as defined above, said miPEP possessing a basic isoelectric point, preferably above 8.

In another aspect, the subject-matter of application FR 13 60727 relates to a nucleic acid molecule encoding a miPEP as defined above.

In other aspect, the subject-matter of application FR 13 60727 relates to a vector comprising at least one nucleic acid molecule as defined above.

In another aspect, the subject-matter of application FR 13 60727 also relates to the use of at least:
- a miPEP as defined above,
- a nucleic acid encoding said miPEP, or
- a vector containing said nucleic acid, to modulate the expression of at least one gene in a specified eukaryotic cell, said specified eukaryotic cell being capable of expressing a microRNA the primary transcript of which contains at least one nucleotide sequence encoding said at least one miPEP and the accumulation of which is modulated by said at least one miPEP, the expression of said at least one gene being regulated by said microRNA.

In another aspect, the subject-matter of application FR 13 60727 also relates to the use of at least:
- a miPEP of 4 to 100 amino acids, preferably of 4 to 40 amino acids, encoded by a nucleotide sequence contained in the primary transcript of a microRNA, said miPEP being capable of modulating the accumulation of said microRNA in a eukaryotic cell,
- a nucleic acid encoding said miPEP, or
- a vector containing said nucleic acid, to modulate the expression of at least one gene in a specified eukaryotic cell, said specified eukaryotic cell being capable of expressing a microRNA the primary transcript of which contains at least one nucleotide sequence encoding said at least one miPEP and the accumulation of which is modulated by said at least one miPEP, the expression of said at least one gene being regulated by said microRNA.

The subject-matter of application FR 13 60727 is based on the inventors' surprising observation that it is possible to modulate the expression of one or more target genes of one and the same microRNA by modulating the accumulation of said microRNA using a miPEP.

In an embodiment, the subject-matter of application FR 13 60727 relates to the use as defined above in which said specified eukaryotic cell is a plant cell.

In an embodiment, the subject-matter of application FR 13 60727 relates to the use as defined above in which said microRNA and said gene are of endogenous origin in said specified eukaryotic cell.

In an embodiment, the subject-matter of application FR 13 60727 relates to the use as defined above in which said microRNA and said gene are of exogenous origin in said specified eukaryotic cell, said specified eukaryotic cell containing at least one vector allowing the expression of said microRNA and of said gene.

In application FR 13 60727, the expressions "of endogenous origin" and "of exogenous origin" are used for distinguishing said microRNAs and/or the genes of different species, assuming conservation of the sequences between species.

Thus, the term "of endogenous origin" indicates that the microRNA and/or gene can be present naturally in the cell in question. However, other copies of the microRNA and/or of the gene of endogenous origin can be added artificially to the cell in question, for example by cloning.

Conversely, the term "of exogenous origin" indicates that the microRNA and/or gene are never present naturally in the cell in question. It is a microRNA and/or a gene identified in another cellular type or in an organism of another species; this microRNA and/or this gene are therefore necessarily introduced artificially into the cell in question.

In application FR 13 60727, a genetically transformed cell can therefore contain 2 groups of microRNAs and/or of genes that are potentially close in terms of sequence, one of endogenous origin and the other of exogenous origin.

In another aspect, the subject-matter of application FR 13 60727 relates to a method for modulating the expression of a gene regulated by a microRNA in a eukaryotic cell, comprising carrying out a step of accumulation of a miPEP in said eukaryotic cell, said miPEP having:
- a size of 4 to 100 amino acids, preferably 4 to 20 amino acids, and
- a peptide sequence identical to that encoded by a nucleotide sequence contained in the primary transcript of a microRNA regulating the expression of said gene, and
- being capable of modulating the accumulation of said microRNA, in which the accumulation of said miPEP in said eukaryotic cell induces a modulation of the expression of said gene relative to the expression of said gene without accumulation of said miPEP.

In an embodiment, the subject-matter of application FR 13 60727 relates to a method for modulating the expression of a gene as defined above, in which the accumulation of said miPEP in the cell results from:
- the introduction of a nucleic acid encoding said miPEP into the cell, or
- the introduction of said miPEP into the cell.

In an embodiment, the subject-matter of application FR 13 60727 relates to a method for modulating the expression of a gene as defined above, in which said eukaryotic cell is a plant cell.

In an embodiment, the subject-matter of application FR 13 60727 relates to a method for modulating the expression of a gene as defined above, in which said microRNA and said gene are of endogenous origin in said eukaryotic cell.

In an embodiment, the subject-matter of application FR 13 60727 relates to a method for modulating the expression of a gene as defined above, in which said microRNA and said gene are of exogenous origin in said eukaryotic cell, said eukaryotic cell containing at least one vector allowing the expression of said microRNA and of said gene.

In another aspect, the subject-matter of application FR 13 60727 relates to a modified eukaryotic cell containing a peptide identical to a miPEP as defined above, said peptide being present in said eukaryotic cell independently of the transcription of the primary transcript of the microRNA bearing the nucleotide sequence encoding said miPEP.

In application FR 13 60727, the term "modified eukaryotic cell" means that said eukaryotic cell contains a miPEP introduced artificially into the cell, whether it is as a peptide, or via a vector encoding said miPEP.

In an embodiment, the subject-matter of application FR 13 60727 relates to a modified eukaryotic cell as defined above, in which said microRNA is of endogenous origin.

In another embodiment, the subject-matter of application FR 13 60727 relates to a modified eukaryotic cell as defined above, in which said microRNA is of exogenous origin, said modified eukaryotic cell containing a vector allowing the expression of said microRNA.

In an embodiment, the subject-matter of application FR 13 60727 relates to a modified eukaryotic cell as defined above, said cell being a plant cell.

In another aspect, the subject-matter of application FR 13 60727 relates to a plant comprising at least one modified eukaryotic cell as defined above.

In another aspect, the subject-matter of application FR 13 60727 relates to a composition comprising at least:
- a miPEP as defined above,
- a nucleic acid encoding said miPEP, or
- a vector containing said nucleic acid.

In another aspect, the subject-matter of application FR 13 60727 relates to a pesticide composition comprising at least:
- a miPEP as defined above,
- a nucleic acid encoding said miPEP, or
- a vector containing said nucleic acid.

In another aspect, the subject-matter of application FR 13 60727 relates to a phytopharmaceutical composition comprising at least:
- a miPEP as defined above,
- a nucleic acid encoding said miPEP, or
- a vector containing said nucleic acid.

In another aspect, the subject-matter of application FR 13 60727 relates to an eliciting composition comprising at least:
- a miPEP as defined above,
- a nucleic acid encoding said miPEP, or
- a vector containing said nucleic acid.

By "eliciting composition" is meant a composition capable of giving the plant a better capacity for symbiosis or a better resistance to various stresses, whether they are of a thermal, hydric or chemical nature.

To this end, the subject-matter of application FR 13 60727 also relates to compositions acting on the plant's growth (inhibition of growth or conversely increase in growth) and physiology (better capacity for formation of mycorrhizae and nodulation, better tolerance to various stresses).

In another aspect, the subject-matter of application FR 13 60727 relates to a herbicide composition comprising at least:
- a miPEP as defined above,
- a nucleic acid encoding said miPEP, or
- a vector containing said nucleic acid.

In another aspect, the subject-matter of application FR 13 60727 relates to an insecticide composition comprising at least:
- a miPEP as defined above,
- a nucleic acid encoding said miPEP, or
- a vector containing said nucleic acid.

In another aspect, the subject-matter of application FR 13 60727 relates to the use of a composition as defined above, as a herbicide for eliminating the plants or slowing their growth, preferably as a herbicide specific to a species or to a genus of plants.

In another aspect, the subject-matter of application FR 13 60727 relates to the use of a composition as defined above, as a phytopharmaceutical,
for promoting the growth and/or the development of plants, in particular for modulating the physiological parameters of a plant, in particular the biomass, leaf surface area, flowering, size of the fruit, production and/or selection of plant seeds, in particular for controlling a plant's parthenocarpy or monoecism, or for modifying the physiological parameters of plant seeds, in particular the germination, establishment of the roots, and resistance to water stress,
or for preventing or treating plant diseases, in particular for promoting resistance to infectious diseases.

In another aspect, the subject-matter of application FR 13 60727 relates to the use of a composition as defined above, for modulating the physiological parameters of a plant, in particular the biomass, leaf surface area, or size of the fruit.

In an embodiment, the subject-matter of application FR 13 60727 relates to the use of a composition as defined above, for thinning orchards in order to increase the size of the fruit.

In an embodiment, the subject-matter of application FR 13 60727 relates to the use of a composition as defined above, for the production and/or selection of plant seeds, said composition being used for controlling a plant's parthenocarpy or monoecism.

In an embodiment, the subject-matter of application FR 13 60727 relates to the use of a composition as defined above, said composition being administered to said plant via the leaves or via the roots.

In an embodiment, the subject-matter of application FR 13 60727 relates to the use of a composition as defined above, for the production and/or selection of plant seeds.

In an embodiment, the subject-matter of application FR 13 60727 relates to the use of a composition as defined above, in which said composition is used for modifying the physiological parameters of said plant seeds, in particular establishment of the roots, germination and resistance to water stress.

In an embodiment, the subject-matter of application FR 13 60727 relates to the use of a composition as defined above, in which said composition is applied by coating or forming a film on said plant seeds.

In another aspect, the subject-matter of application FR 13 60727 relates to the use of a composition as defined above, as a pesticide for eliminating organisms that are harmful to the plants or that can be classified as such, in particular as insecticide, arachnicide, molluscicide or rodenticide.

In an embodiment, the subject-matter of application FR 13 60727 relates to the use of a composition as defined above, as insecticide.

In an embodiment, the subject-matter of application FR 13 60727 relates to the use of a composition as defined above, for eliminating insect pests.

In an embodiment, the subject-matter of application FR 13 60727 relates to the use of a composition as defined above, for eliminating animal species that are classified as harmful or that can be classified as such, in particular the Muridae, in particular the rat.

In another aspect, the subject-matter of application FR 13 60727 relates to the use of a composition as defined above, in which said composition is applied onto a plant to protect it against insect pests.

The following figures and examples will better illustrate the invention, without limiting its scope.

CAPTIONS TO THE FIGURES

FIG. 1. Effects of the overexpression of miR171b (miR171b identified in *Medicago truncatula*) on the expression of the HAM1 and HAM2 (A) genes or on the number of lateral roots (B) in *M. truncatula*.

(A) The y-axis shows the relative expression of miR171b (left columns), of HAM1 (centre columns) or of HAM2 (right columns) in a control plant (white columns) or in a plant in which miR171b is overexpressed (black columns). The error bar corresponds to the standard error of the mean (number of individuals=10). The overexpression of miR171b causes a reduction in the expression of the HAM1 and HAM2 genes.

(B) The y-axis shows the average number of lateral roots observed in a control plant (white column) or in a plant in which miR171b is overexpressed (black column). The error bar corresponds to the standard error of the mean (number of individuals=100). The overexpression of miR171b leads to a reduction in the number of lateral roots.

Figure 2:
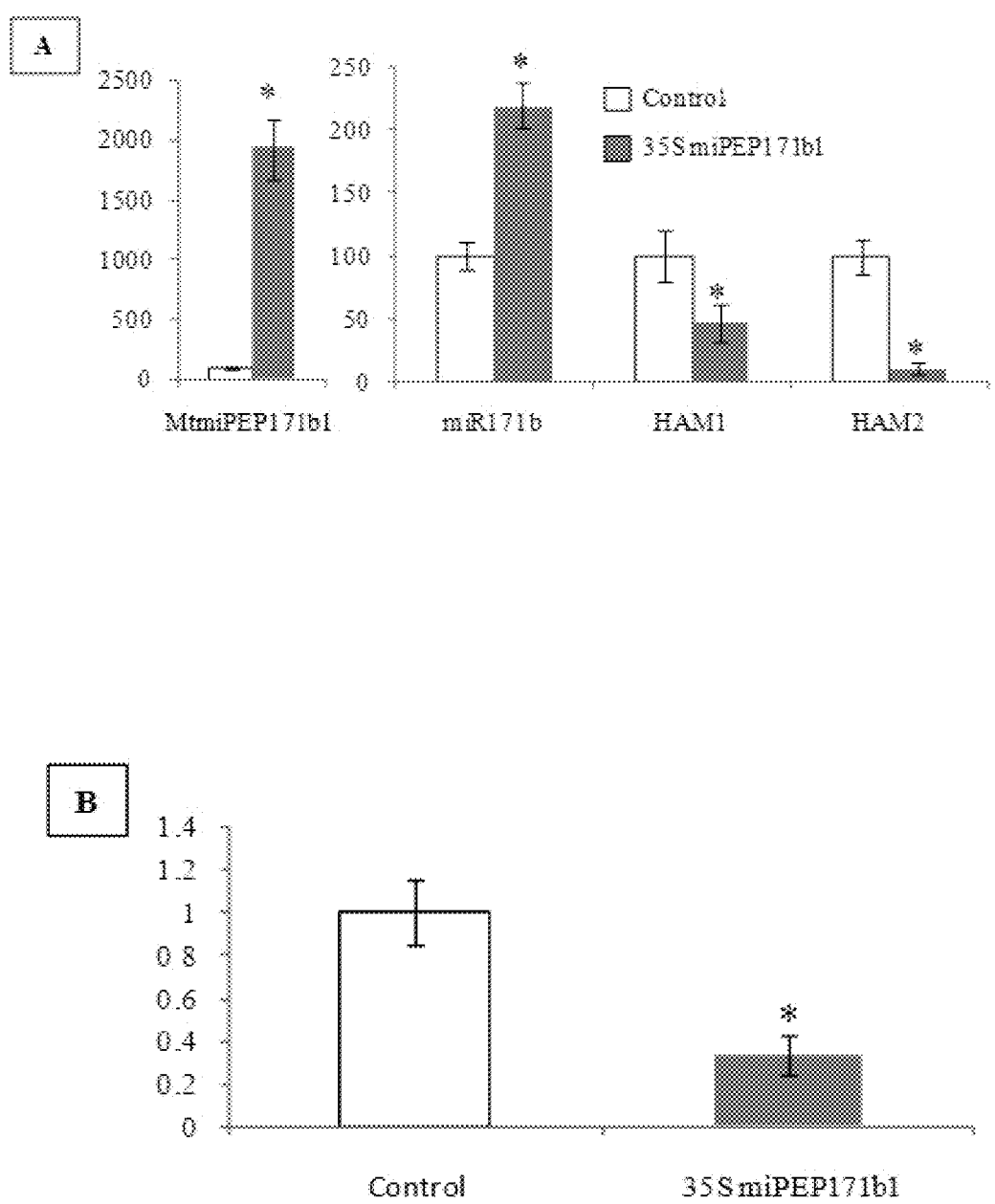

FIG. 2. Effects of the overexpression of miPEP171b on the expression of miR171b and of the HAM1 and HAM2 (A) genes or on the number of lateral roots (B) in *M. truncatula*.

(A) The y-axis shows the relative expression of miPEP171b (graph on the left), of miR171b (graph on the right, left columns), of HAM1 (accession No. MtGI9-TC114268) (graph on the right, centre columns) or of HAM2 (accession No. MtGI9-TC120850) (graph on the right, right columns) in a control plant (white columns) or in a plant in which miPEP171b is overexpressed (black columns). The error bar corresponds to the standard error of the mean (number of individuals=10). The overexpression of miPEP171b causes an increase in the accumulation of miR171b, as well as a reduction in the expression of the genes HAM1 and HAM2.

(B) The y-axis shows the average number of lateral roots observed in a control plant (white column) or in a plant in which miPEP171b is overexpressed (black column). The error bar corresponds to the standard error of the mean (number of individuals=100). The overexpression of miPEP171b leads to a reduction in the number of lateral roots.

Figure 3:
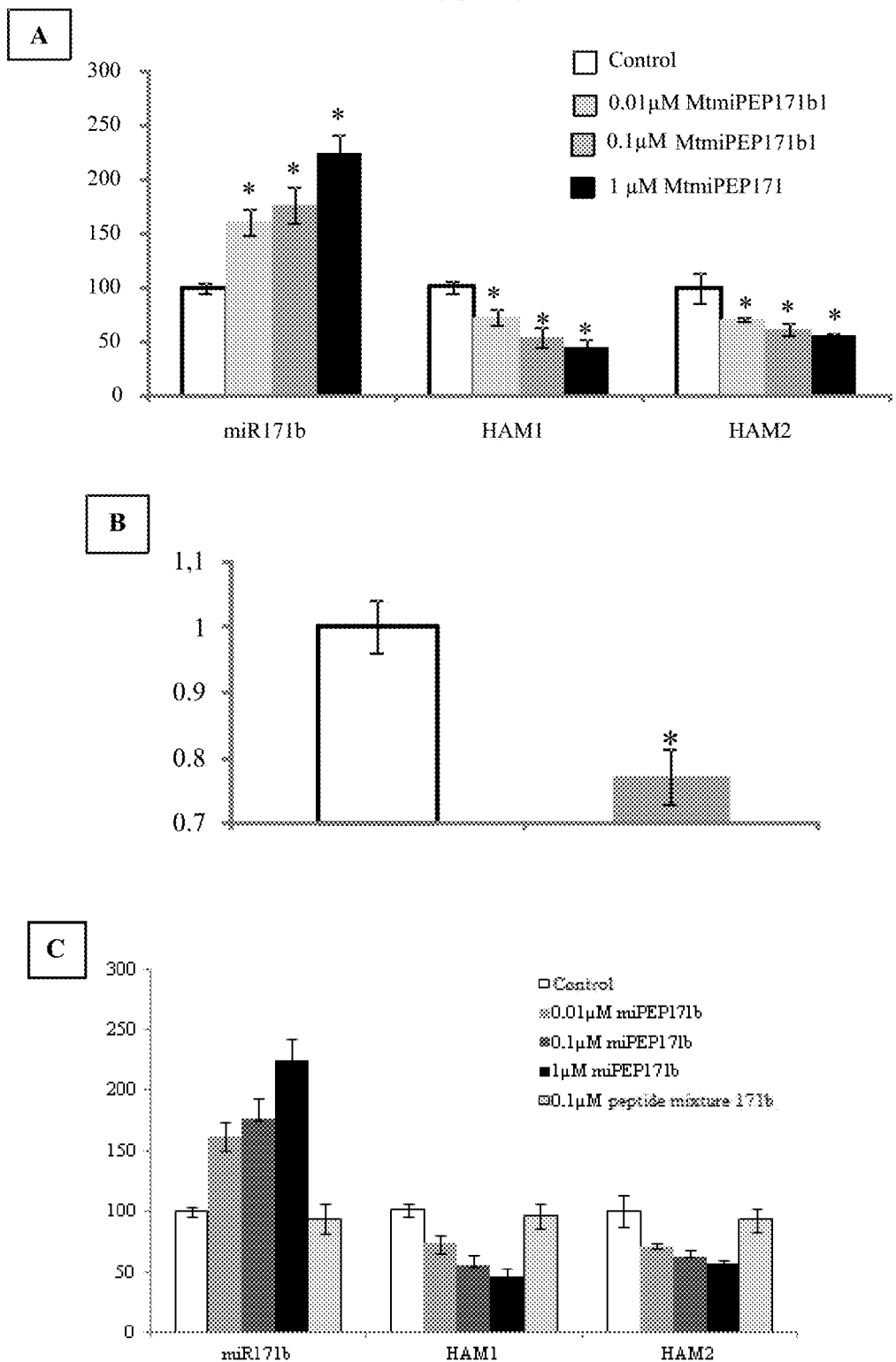

FIG. 3. Effects of miPEP171b on the expression of miR171b and of the genes HAM1 and HAM2 (A) and on the number lateral roots (B) in *M. truncatula*.

(A) The y-axis shows the relative expression of miR171b (left columns), of HAM1 (centre columns) or of HAM2 (right columns) in a control plant (white columns) or in a plant grown on a medium containing miPEP171b at 0.01 µM (light grey columns), 0.1 µM (dark grey columns) or 1 µM (black columns). The error bar corresponds to the standard error of the mean (number of individuals=10). The application of miPEP171b to the different concentrations causes an increase in the accumulation of miR171b, as well as a reduction in the expression of the HAM1 and HAM2 genes.

(B) The y-axis shows the average number of lateral roots observed in a control plant (white column) or in a plant grown on medium containing miPEP171b at 0.1 µM for 5 days and 1 time per day (black column). The error bar corresponds to the standard error of the mean (number of individuals=100). The application of miPEP171b at 0.1 µM leads to a reduction in the number of lateral roots.

(C) The y-axis shows the relative expression of MtmiR171b (left columns), of HAM1 (centre columns) or of HAM2 (right columns) in a control plant (white columns) or in a plant treated by watering for 5 days and 1 time per day with MtmiPEP171b1 at 0.01 µM (grey columns), 0.1 µM (dark grey columns) or 1 µM (black columns) or with 0.01 µM of a peptide mixture (light grey columns) the composition of amino acids of which is identical to miPEP171b but the sequence of which is different. The error bar corresponds to the standard error of the mean (number of individuals=10).

Figure 4:
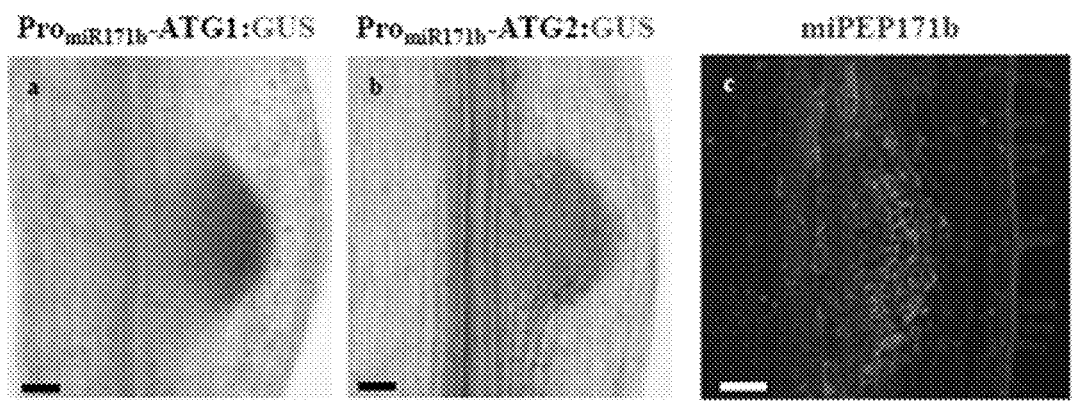

FIG. 4. Immunolocalization

The roots of *Medicago truncatula* were transformed in order to express fusions between the protein GUS (in blue) and the ATG of miPEP171b (Pro$_{miR171b}$-ATG1:GUS) or the ATG2 (second ATG being located on the precursor, after the miPEP) (Pro$_{miR171b}$-ATG2:GUS). Labelling was also carried out with an antibody anti-miPEP171b (miPEP171b). The immunolocalization of miPEP171b in the roots of *M. truncatula* reveals the presence of miPEP171b in the initiation sites of the lateral roots, showing a co-localization between the microRNA and the corresponding miPEP.

Figure 5:
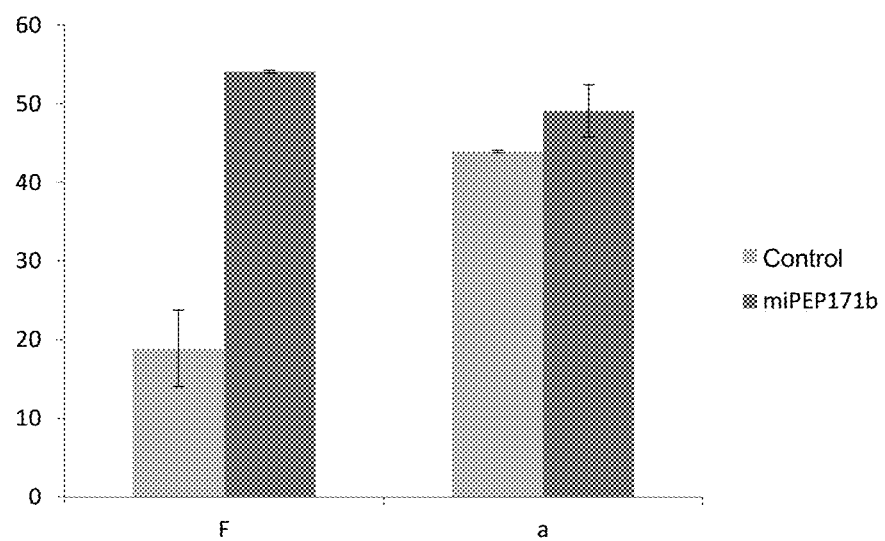

FIG. 5. Effects of miPEP171b on the colonization of *M. truncatula* by the fungus *Rhizophagus irregularis*

The y-axis shows the percentage colonization (on the left) and the abundance of the arbuscules (on the right) in roots of *M. truncatula* treated with a solvent (control, light bars) or with a solvent containing 0.1 µM of miPEP171b (miPEP171b, dark bars). The error bar corresponds to the standard error of the mean (number of individuals=15).

Figure 6:
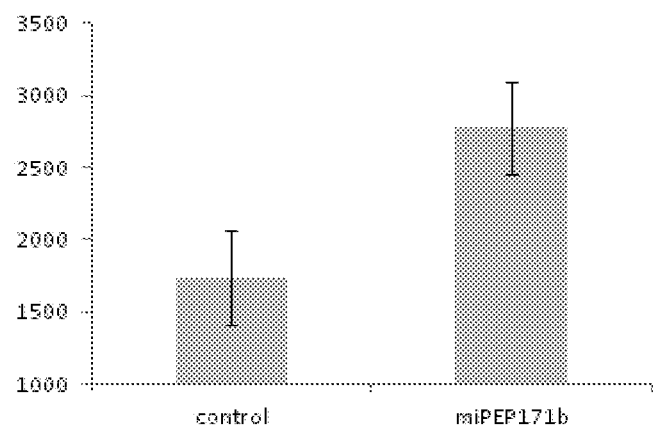

FIG. 6. Effects of miPEP171b on the surface area of the arbuscules formed by the fungus *Rhizophagus irregularis* in *M. truncatula*

The y-axis shows the surface area of the arbuscules (measured in arbitrary units) in roots of *M. truncatula* treated with a solvent (control) or with a solvent containing 0.1 µM of miPEP171b (miPEP171b).

The error bar corresponds to the standard error of the mean (number of individuals=15).

Figure 7:
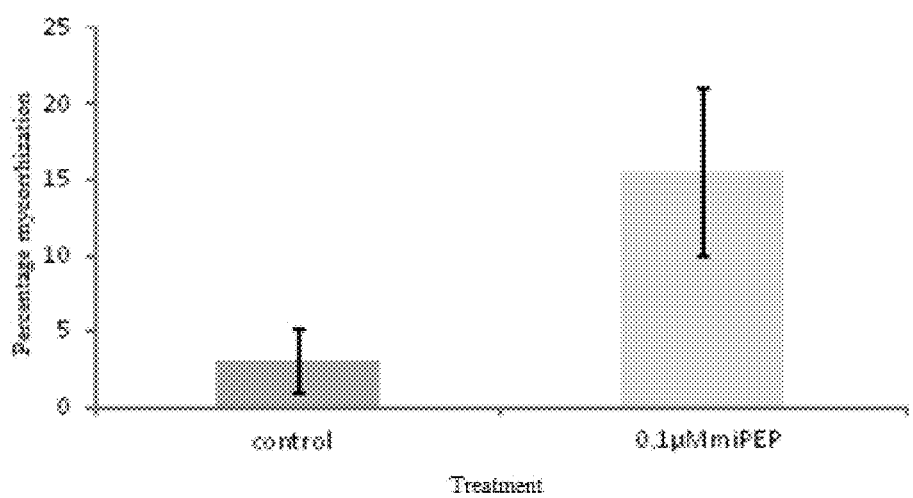

FIG. 7. Effect of miPEP171b on the mycorrhization rate of *M. truncatula* by the fungus *Rhizophagus irregularis*

The y-axis shows the mycorrhization rate in roots of *M. truncatula* treated 5 weeks post inoculation with a solvent (left bar) or with a solvent containing 0.1 µM of miPEP171b (miPEP, right bar).

The error bar corresponds to the standard error of the mean (number of individuals=12).

Figure 8:
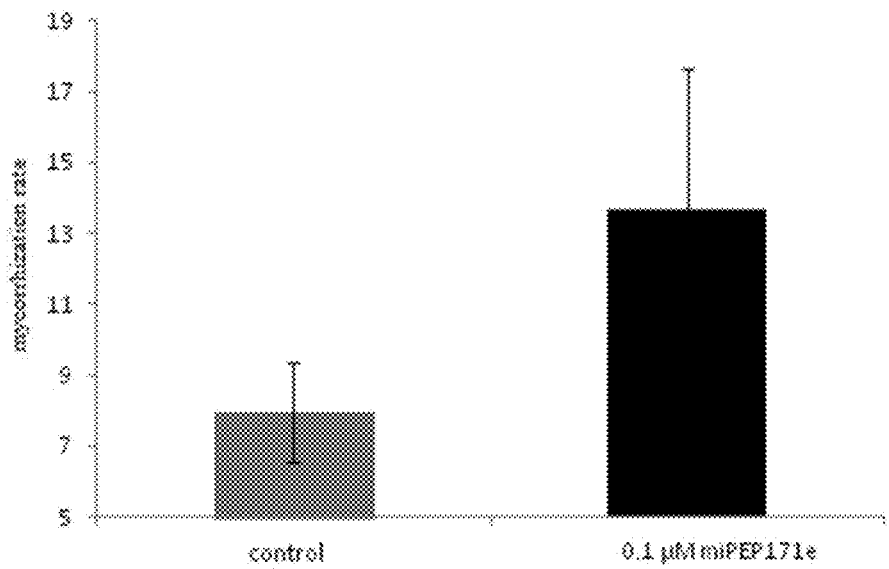

FIG. 8. Effect of slmiPEP171e on the mycorrhization rate of *Solanum lycopersicum*

The y-axis shows the mycorrhization rate of *Solanum lycopersicum* plants treated 12 weeks post inoculation with a solvent (left bar) or with a solvent containing 0.1 µM of slmiPEP171e (miPEP, right bar).

The error bar corresponds to the standard error of the mean (number of individuals=12).

Figure 9:
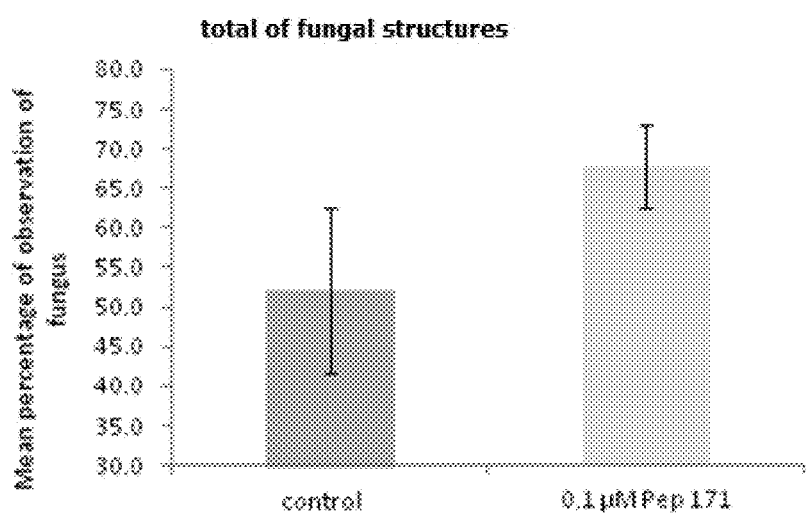

FIG. 9. Effects of ljmiPEP171b on the number of fungal structures in *Lotus japonicus*

The y-axis shows the number of fungal structures in a plant treated 5 weeks post inoculation with a solvent (left bar) or with a solvent containing 0.1 µM of ljmiPEP171b (Pep 171, right bar).

The error bar corresponds to the standard error of the mean (number of individuals=10 control plants, 12 treated plants).

Figure 10:
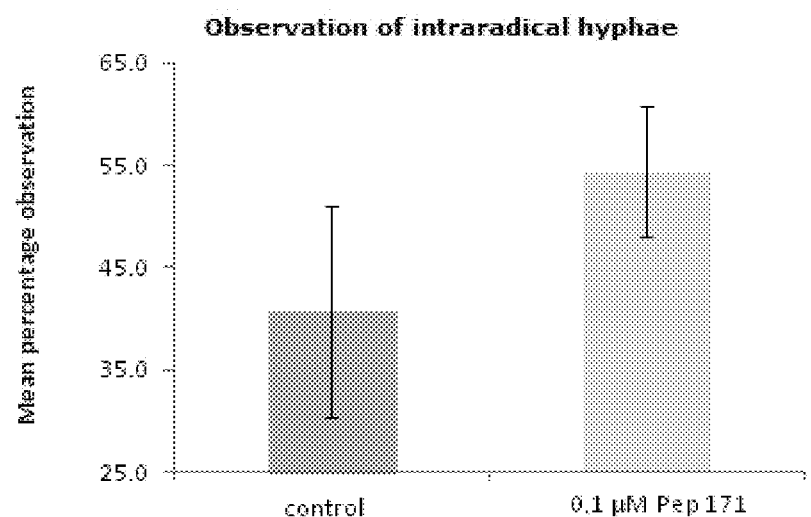

FIG. 10. Effects of ljmiPEP171b on the number of intraradical hyphae in *Lotus japonicus*

The y-axis shows the number of intraradical hyphae in a plant treated 5 weeks post inoculation with a solvent (left bar) or with a solvent containing 0.1 µM of ljmiPEP171b (Pep 171, right bar).

The error bar corresponds to the standard error of the mean (number of individuals=10 control plants, 12 treated plants).

Figure 11:
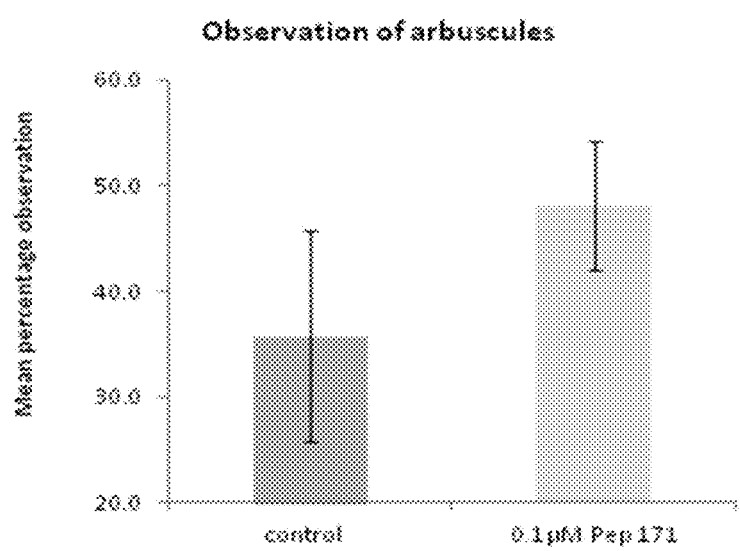

FIG. 11. Effects of ljmiPEP171b on the number of arbuscules in *Lotus japonicus*

The y-axis shows the number of arbuscules in a plant treated 5 weeks post inoculation with a solvent (left bar) or with a solvent containing 0.1 µM of ljmiPEP171b (Pep 171, right bar).

The error bar corresponds to the standard error of the mean (number of individuals=10 control plants, 12 treated plants).

Figure 12:
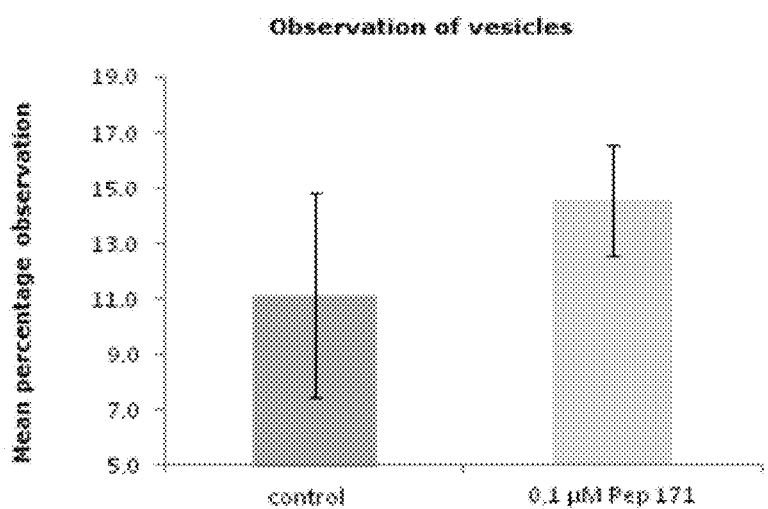

FIG. 12. Effects of the ljmiPEP171b on the number of vesicles in *Lotus japonicus*

The y-axis shows the number of vesicles in a plant treated 5 weeks post inoculation with a solvent (left bar) or with a solvent containing 0.1 µM of ljmiPEP171b (Pep 171, right bar). The error bar corresponds to the standard error of the mean (number of individuals=10 control plants, 12 treated plants).

Figure 13:
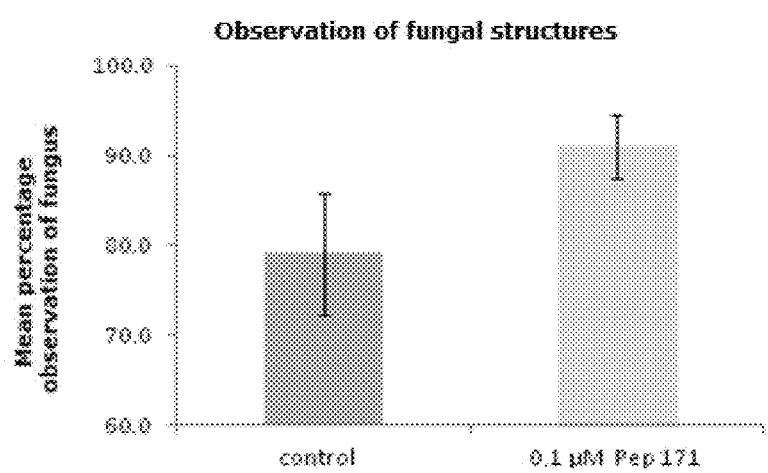

FIG. 13. Effects of the osmiPEP171i on the number of fungal structures in *Oryza sativa*

The y-axis shows the number of fungal structures in a plant treated 5 weeks post inoculation with a solvent (left bar) or with a solvent containing 0.1 µM of ljmiPEP171b (Pep 171, right bar).

The error bar corresponds to the standard error of the mean (number of individuals=5 control plants, 5 treated plants).

Figure 14:
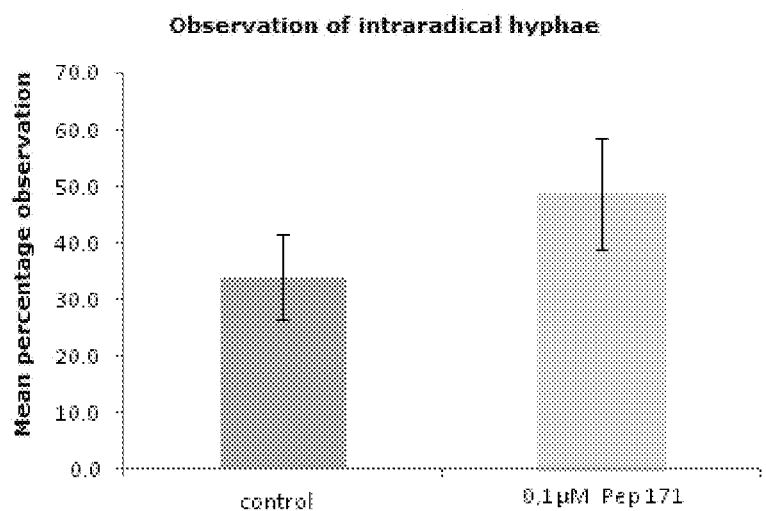

FIG. 14. Effects of osmiPEP171i on the number of intraradical hyphae in *Oryza sativa*

The y-axis shows the number of intraradical hyphae in a plant treated 5 weeks post inoculation with a solvent (left bar) or with a solvent containing 0.1 µM of ljmiPEP171b (Pep 171, right bar).

The error bar correspond to the standard error of the mean (number of individuals=5 control plants, 5 treated plants).

Figure 15:
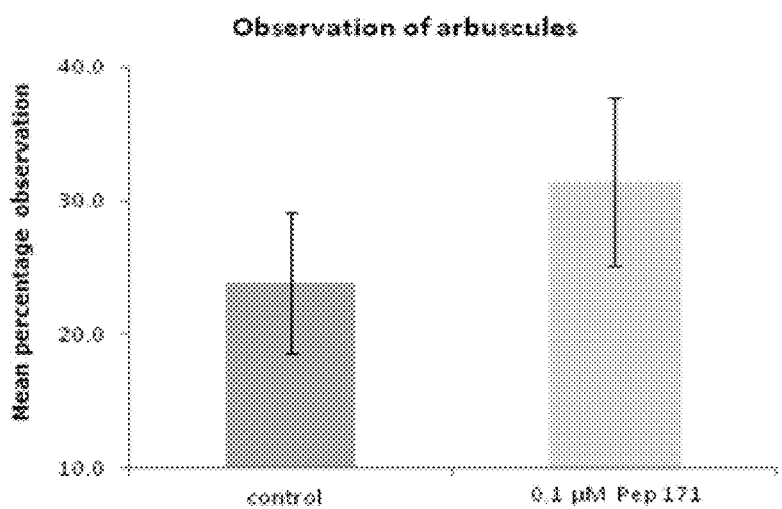

FIG. 15. Effects of osmiPEP171i on the number of arbuscules in *Oryza sativa*

The y-axis shows the number of arbuscules in a plant treated 5 weeks post inoculation with a solvent (left bar) or with a solvent containing 0.1 µM of ljmiPEP171b (Pep 171, right bar).

The error bar corresponds to the standard error of the mean (number of individuals=5 control plants, 5 treated plants).

Figure 16:
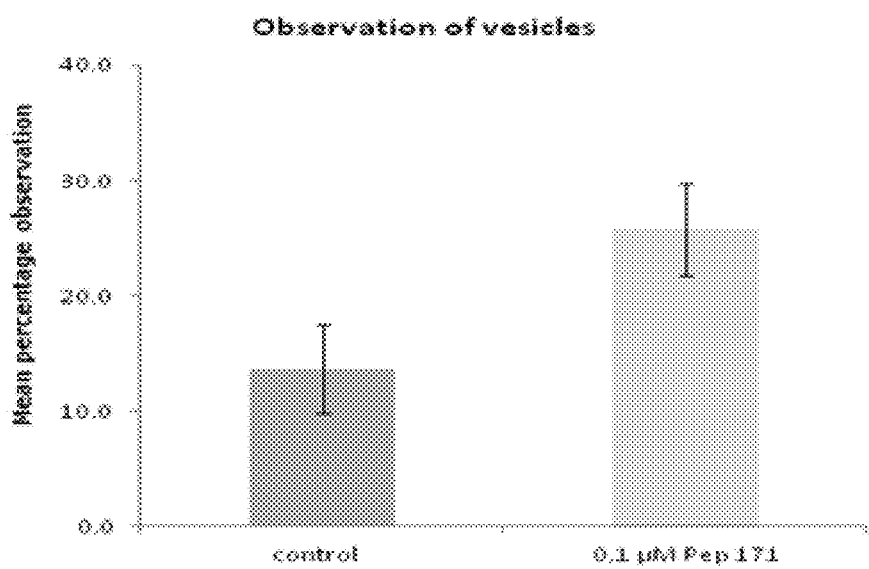

FIG. 16. Effects of osmiPEP171i on the number of vesicles in *Oryza* sativa

The y-axis shows the number of vesicles in a plant treated 5 weeks post inoculation with a solvent (left bar) or with a solvent containing 0.1 µM of OsmiPEP171i (Pep 171, right bar).

The error bar corresponds to the standard error of the mean (number of individuals=5 control plants, 5 treated plants).

Figure 17:
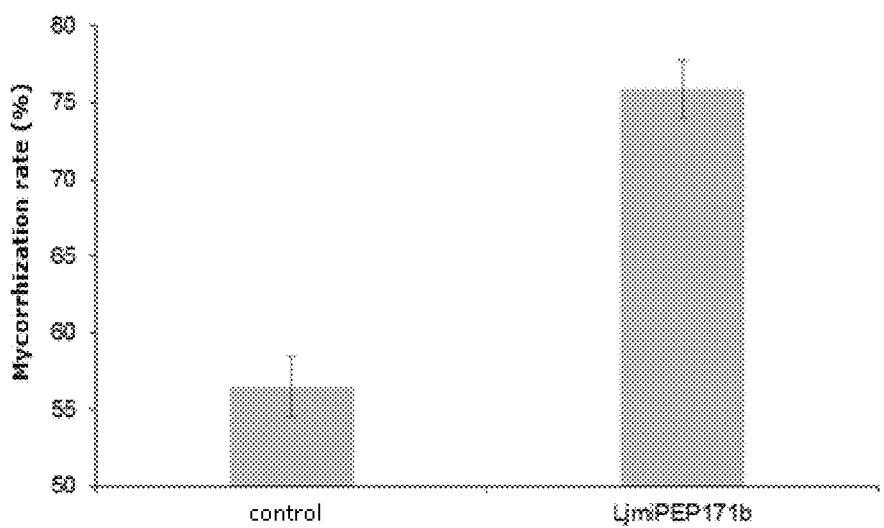

FIG. 17. Effects of slmiPEP171e on the mycorrhization rate of *Solanum lycopersicum*

The y-axis shows the mycorrhization rate of *Solanum lycopersicum* plants treated 12 weeks post inoculation with a solvent (left bar) or with a solvent containing 0.1 µM of slmiPEP171e (right bar).

The error bar corresponds to the standard error of the mean (number of individuals=12).

Figure 18:
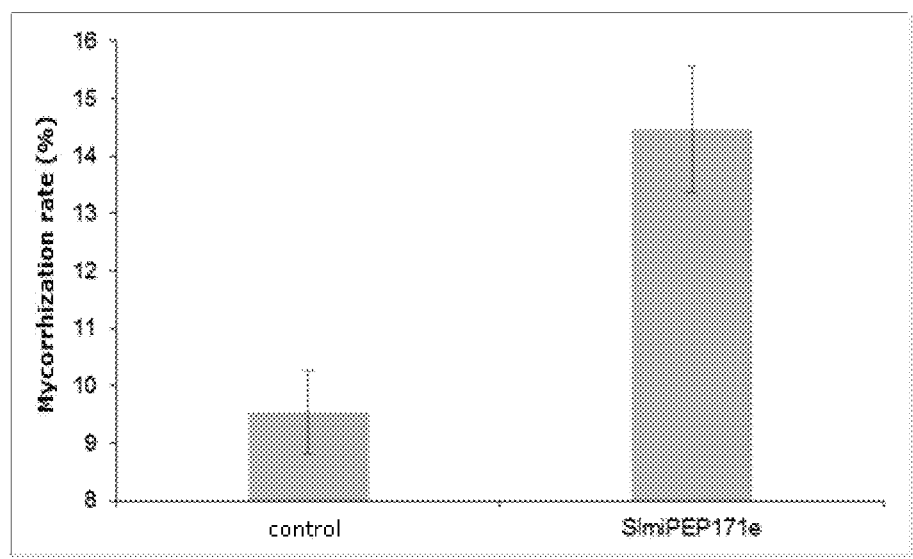

FIG. 18. Effects of ljPEP171b on the mycorrhization rate of *Lotus japonicus*

The y-axis shows the mycorrhization rate of *Lotus japonicus* plants treated 5 weeks post inoculation with a solvent (left bar) or with a solvent containing 0.1 µM of ljmiPEP171b (right bar).

The error bar corresponds to the standard error of the mean (number of individuals=12).

Figure 19:
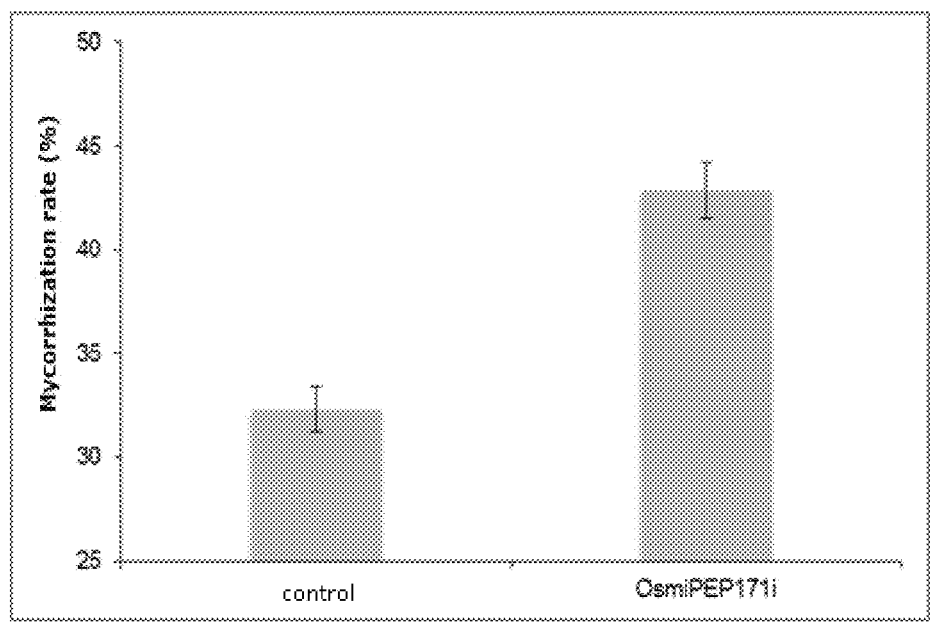

FIG. 19. Effects of OsPEP171i on the mycorrhization rate of *Oricea sativa*

The y-axis shows the mycorrhization rate of *Oryza sativa* plants treated 5 weeks post inoculation with a solvent (left bar) or with a solvent containing 0.1 µM of OsmiPEP171i (right bar).

The error bar corresponds to the standard error of the mean (number of individuals=12).

EXAMPLES

Example 1—Identification and Characterization of miPEP171b

MiR171b is expressed in the meristematic region of the roots, as well as in the initiation sites of the lateral roots. The overexpression of this miRNA leads in particular to a reduction in the expression of the HAM1 genes (Accession No. MtGI9-TC114268) and HAM2 genes (Accession No. MtGI9-TC120850) (FIG. 1A), as well as a reduction in the number of lateral roots (FIG. 1B).

The sequence of the primary transcript of the miR171b was determined by using the RACE-PCR technique. Analysis of the sequence of the primary transcript made it possible to identify the presence of several small open reading frames (ORF) that were completely unexpected.

The overexpression of the first ORF, called miORF171b, leads to an increase in the accumulation of miR171b and a reduction in the expression of the HAM1 and HAM2 genes (see FIG. 2A), as well as to a reduction in the number of lateral roots (FIG. 2B), as was already observed during the overexpression of miR171b.

In order to determine if miORF171b leads to the actual production of a peptide an immunolocalization of the peptide with a specific antibody was carried out and revealed the presence of the peptide in the initiation sites of the lateral roots, thus showing a co-localization between the microRNA and the corresponding miPEP. In order to determine if the regulation function noted is in fact shown by said peptide, a synthetic peptide, the sequence of which is identical to that potentially encoded by miORF171b, was applied to the roots of *Medicago truncatula*. The application of this peptide leads to the phenotype already noted above during the overexpression of miORF171b, i.e. it leads to an increase in the accumulation of miR171b and a reduction in the expression of the HAM1 and HAM2 genes (see FIG. 3A), as well as a reduction in the number of lateral roots (FIG. 3B). The results of these experiments demonstrate that the miORF171b encoded a peptide capable of modulating the accumulation of miR171b, and the expression of the target genes miR171b: HAM1 and HAM2. Said peptide was called miPEP171b.

Moreover, the immunolocalization of miPEP171b1 in the roots of *M. truncatula* reveals the presence of miPEP171b1 in the initiation sites of the lateral roots, showing a co-localization between the microRNA and the corresponding miPEP.

Example 2—Effects of miPEP171b on Mycorrhization in *M. truncatula*

*Medicago truncatula* plants were treated for 5 weeks, by watering every 2 days, with low concentrations (0.1 µM) of a synthetic peptide the sequence of which is identical to that of miPEP171b, and the percentage colonization of the plant was measured.

The results of these experiments indicate that the treatment with the miPEP171b significantly increased the mycorrhization in *M. truncatula* (FIG. 5).

Moreover, it was observed that the arbuscules obtained in the roots treated with miPEP171b have a larger size than those present in the control roots not treated with miPEP171b (FIG. 6).

It was also observed that the mycorrhization rate is greater in the plants treated with miPEP171b relative to the control plants not treated with miPEP171b (FIG. 7).

Example 3—Effects of miPEP171b on Mycorrhization in *Medicago sativa*

The homologue of the miPEP171b of *M. truncatula* was identified in *M. sativa* by BLAST and RACE PCR.

A treatment with different doses of miPEP171b (0.01 μM to 10 μM) is carried out in parallel with the mycorrhization of *M. sativa*.

Example 4—Effects of miPEP171b on Mycorrhization in *Glycine max* (Soya)

The homologue of the miPEP171b of *M. truncatula* was identified in soya by BLAST and RACE PCR.

A treatment with different doses of miPEP171b (0.01 μM to 10 μM) is carried out in parallel with mycorrhization of the soya.

Example 5—Effects of slmiPEP171e on Mycorrhization in *Solanum lycopersicum* (Tomato)

The homologue of the miPEP171e of *M. truncatula* was identified in the tomato by BLAST and RACE PCR.

The effects of slmiPEP171e on mycorrhization of the tomato were analyzed by treating the plants with slmiPEP171e in parallel with the mycorrhization.

The results are shown in FIGS. 8 and 17.

These results indicate that slmiPEP171e promotes the mycorrhization of the tomato.

Example 6—Effects of LjmiPEP171b on Mycorrhization in *Lotus japonicus* (Birdsfoot Trefoil)

The homologue of the miPEP171b of *M. truncatula* was identified in birdsfoot trefoil by BLAST and RACE PCR.

The effects of the LjmiPEP171b on mycorrhization of the birdsfoot trefoil were analyzed by treating the plants with LjmiPEP171b in parallel with the mycorrhization.

The results are shown in FIGS. 9, 10, 11, 12 and 18.

These results indicate that LjmiPEP171b promotes the mycorrhization of birdsfoot trefoil.

Example 7—Effects of osmiPEP171i on Mycorrhization in *Oryza sativa* (Rice)

The homologue of the miPEP1 71i of *M truncatula* was identified in rice by BLAST and RACEPCR.

The effects of the osmiPEP171i on mycorrhization of the rice were analyzed by treating the plants with osmiPEP171i in parallel with the mycorrhization.

The results are shown in FIGS. 13, 14, 15, 16 and 19. These results indicate that osmiPEP171i promotes the mycorrhization of birdsfoot trefoil rice.

Material and Methods

*Medicago truncatula*

Biological Material

The surface of the seeds of *M. truncatula* was sterilized and they were placed to germinate on agar plates for 5 days at 4° C. in the dark. The young shoots were then grown on 12 cm square plates filled with Fahraeus medium without nitrogen and containing 7.5 μM phosphate (Lauresergues et al., *Plant J.*, 72(3):512-22, 2012). The lateral roots were counted every day. In pots, the plants were watered every two days with modified Long Ashton medium containing little phosphorus (Balzergue et al., 2011 *Journal of experimental botany*, 62:1049-1060).

The peptides were synthesized by Eurogentec or Smartox-Biotech. The miPEP171b was placed in suspension in a water 40%/acetonitrile 50%/acetic acid 10% (v/v/v) solution.

Reverse Transcription of the microRNAs

The RNA was extracted by using the reagent Tri-Reagent (MRC) according to the manufacturer's instructions, with the exception of precipitation of the RNA which was carried out with 3 volumes of ethanol. The reverse transcription of the RNA was carried out by using the specific stem-loop primer RTprimer171b in combination with hexamers for carrying out the reverse transcription of the RNA of high molecular weight.

In brief, 1 μg of RNA was added to the stem-loop primer MIR171b (0.2 μM), the hexamer (500 ng), the buffer RT (1×), the SuperScript Reverse transcriptase (SSIII) enzyme (one unit), the dNTPs (0.2 mM each), the DTT (0.8 mM) in a final reaction mixture of 25 μl. In order to carry out the reverse transcription, a pulsed reverse transcription reaction was carried out (40 repetitions of the following cycle: 16° C. for 2 minutes, 42° C. for one minute and 50° C. for one second, followed by a final inactivation of the reverse transcription at 85° C. for 5 minutes).

Analyses by Quantitative RT-PCR (qRT-PCR)

The total RNA of the roots of *M. truncatula* was extracted by using the RNeasy Plant Mini Kit extraction kit (Qiagen). The reverse transcription was carried out by using the reverse transcriptase SuperScript II (Invitrogen) starting from 500 ng of total RNA. Three repetitions (n=3) were carried out, each with two technical repetitions. Each experiment was repeated from two to three times. The amplifications by qPCR were carried out by using a LightCycler 480 System (Roche Diagnostics) thermocycler according to the method described in Lauressergues et al. (*Plant J.*, 72(3): 512-22, 2012).

Statistical Analyses

The mean values of the relative expression of the genes or of the production of lateral roots were analyzed by using the Student test or the Kruskal-Wallis test. The error bars represent the standard error of the mean (SEM). The asterisks indicate a significant difference (p<0.05).

Plasmid Constructions

The DNA fragments of interest were amplified with Pfu polymerase (Promega). The DNA fragments were cloned using the XhoI and NotI enzymes in a pPEX-DsRED plasmid for an overexpression under the control of the strong constitutive promoter 35S, and using the KpnI-NcoI enzymes in a pPEX GUS plasmid for the reporter genes, according to the method described in Combier et al. (*Genes & Dev*, 22: 1549-1559, 2008).

Transformation of the Plants

The composite plants having roots transformed with *Agrobacterium Rhizogenes* were obtained by the method described in Boisson-Dernier et al. (Mol *Plant-Microbe Interact*, 18:1269-1276, 2005). The transformed roots were verified and selected by observations of DsRED with a binocular fluorescence magnifier. The control roots correspond to roots transformed with *A. rhizogenes* not containing the pPEX-DsRED vector.

Mycorrhization

Sterile spores of *Rhizophagus irregularis* (previously called *Glomus intraradices*) DAOM197198 were purchased from Agronutrition (Carbonne, France).

Seeds of *M. truncatula* (Gaertn 'Jemalong' genotype A17) were sterilized on the surface and placed to germinate on agar plates in the dark for 5 days at 4° C. The plants were then grown on an Oil-Dri US-special substrate (Damolin, Denmark) for 5 to 12 weeks in a growing room and watered every 2 days with modified Long Ashton medium containing a low concentration of phosphate (Balzergue et al., *J Exp Bot,* 62(3):1049-60, 2011).

For the inoculation of the plants with *R. irregularis,* 450 spores were used per plant.

After washing in KOH 10% (weight/volume) and rinsing in sterile water, the mycorrhized roots were treated for 30 minutes with wheat germ agglutinin fluorescein conjugate (Invitrogen) which fixes the fungal chitin, then washed 3 times in a PBS buffer. The roots were then observed with an inverted optical microscope or a confocal microscope (Leica, France).

Alternatively, the roots were labelled with black Schaeffer ink according to the protocol described in Vierheilig et al., *Appl Environ Microbiol,* 64:5004-5007, 1998.

The percentage mycorrhization was measured using grids according to the protocol described in Giovannetti and Mosse, *New Phytol,* 84:489-500, 1980.

The accurate phenotyping of the mycorrhization was also carried out according to the method of Trouvelot et al., *Physiological and Genetical Aspects of Mycorrhizae,* pp 217-221, 1986. The frequency of mycorrhization (F) in the root system and the abundance of the arbuscules (A) (as a percentage) were calculated in colonized root sections using the software Mycocalc.

The size of the arbuscules was measured using the software ImageJ.

Each mycorrhization experiment was carried out at least twice by using 12 plants for each condition, each corresponding to an independent conversion with *A. rhizogenes.*

Immunolocalization

Roots or seedlings of tissues of *Medicago* were fixed for 2 hours in 4% formol (v/v) with 50 mM of phosphate buffer (pH 7.2), then included in LMP agarose 5% in water (with a low melting point). Thin sections (100 µm) were obtained and placed in Pbi (phosphate buffer for immunology) on Teflon-coated slides, blocked in Pbi, 2% Tween and 1% bovine serum albumin for 2 hours (PbiT-BSA), then marked overnight (12 h) at 4° C. with the primary antibody diluted in BSA-PbiT. The sections were washed with PBiT and incubated at ambient temperature for 2 h with a secondary antibody diluted in PbiT-BSA. The slides were then washed in Pbi for 30 min and mounted in citifluor (mounting medium). The primary antibody and the dilutions were as follows: 1716a (1:500, v/v). The secondary antibody was a goat anti-rabbit IgG antibody coupled with the Alexa Fluorine 633 fluorescent probe (Molecular Probes), and was used at a dilution of 1:1000 (v/v).

*S. lycopersicum*

Germination of the Seeds of *S. lycopersicum*

The seeds are sterilized for 2 minutes in sodium hypochlorite solution diluted ¼, then rinsed at least 8 times with sterile water.

The seeds are placed in a Petri dish containing water+1% agar. The dishes are placed at 4° C. overnight, then they are placed at ambient temperature for 4 days in order to germinate the seeds.

Inoculation of the Germinated Seedlings:

The germinated seeds are transferred to an Oil-Dry® substrate containing spores of *Rhizophagus irregularis* at the concentration of 400 spores/L. After two days of adaptation under mini-greenhouse the seedlings are transferred to a growing room or greenhouse. The plants are watered regularly with a solution of Long Ashton+nitrogen (Lauressergues et al., Plant J. 72(3):512-22, 2012).

Treatments of the Plants with miPEP:

The treatment is carried out by watering the plants with 12.5 ml of water+the concentrated solution of miPEP or the equivalent of solvent solution (50% acetonitrile) for the control treatment. The treatments are carried out every two days.

Tomato Root Staining Protocol:

The roots are cleared with 1% KOH 7 minutes at 90° C., then stained 10 minutes in an ink solution (5% Sheaffer ink; 5% acetic acid) at 90° C.

*L. japonicus*

Germination of the Seeds of *L. japonicus:*

The seeds are sterilized in sodium hypochlorite solution for 20 min then rinsed several times in water.

Inoculation of the Germinated Seedlings:

Culturing of the birdsfoot trefoil plants is carried out in a pot containing vermiculite with cotton fibre at the bottom. 5,000 spores of *Rhizophagus irregularis* are added per pot. The spores in mixtures in a substrate are arranged in a layer on the vermiculite to approximately two thirds of the height of the pot. The remainder of the pot is then filled with vermiculite and 10 seeds of pre-germinated birdsfoot trefoil are placed in the moist substrate. 3 pots are prepared for each treatment. The pots are then places in a growing room at 25° C.

Treatments of the Plants with miPEP:

LjmiPEP171e: 0.1 µM (final)

Control: water.

The treatments are carried out on Monday and Friday by mixing the solution of miPEP or control with the nutrient solution (suitable B&D medium) and on Wednesday the solution of miPEP or control in water. Each pot is watered with 10 ml except on Friday 30 ml (without changing the quantity of miPEP), in order to last over the weekend.

Birdsfoot Trefoil Staining Protocol:

Protocol adapted from Vierheilg et al. (1998) (Ink vinegar a simple staining technique for arbuscular-mycorrhizal fungi. *Environ. Microbiol.* 64 (12): 5004-7)

- Cut the roots of the plants inoculated with the mycorrhizal fungus, wash and place them in a 2 ml tube.
- Cover the samples with a solution of 10% KOH and clear the tissues for 15 min at 95° C. in a heating unit. Wear gloves when handling the hot KOH.
- Drain the KOH and rinse the roots once with water and once with 10% acetic acid. Care must be taken not to touch the roots as they are very fragile.
- Cover the roots with a solution of black ink (Pelikan) 5% in a solution of 5% acetic acid. Heat for 5 minutes at 95° C.
- Carefully remove the ink solution with a 200 µL pipette without damaging the roots. Rinse the roots twice with water.
- Clear the roots in a 5% acetic acid solution for 20 minutes under stirring.
- Store at 4° C. until use.
- Mount the roots between slide and cover slip in water or in 50% glycerol.

*O. sativa*

Germination of the Seeds of *O. sativa:*

The seeds are sterilized for 1 min with 70% ethanol, then for 30 min with sodium hypochlorite solution before rinsing.

Inoculation of the Germinated Seedlings:

Culturing of a previously germinated seed of rice is carried out in a pot containing vermiculite with cotton fibre at the bottom. 500 spores of *Rhizophagus irregularis* are added per pot. The spores in mixtures in a substrate are arranged in a layer on the vermiculite at approximately two thirds of the height of the pot. The remainder of the pot is then filled with vermiculite and a hole is made for placing a germinated rice seed therein. The substrate is moistened. The pots are then placed in a growing room at 25° C.

Treatments of the Plants with miPEP:
OsmiPEP171i: 0.1 µM (final)
Control: equivalent of 50% ACN solution
The treatments are carried out on Monday and Friday by mixing the solution of miPEP or control in 60 ml of nutrient solution (1/2 Hoagland with 25 µM Pi and Sequestren) and on Wednesday the solution of miPEP or control in 60 ml of water. Each plant is watered with 10 ml per pot.

Rice Root Staining Protocol:
The roots can be stored in 10% KOH for several months before being stained.
Incubation of the roots for 30 minutes at 96° C. in KOH in a 2 ml tube (with gentle stirring).
Remove the KOH
Rinse three times with water
Incubate in 0.3M HCl for 15 min to 2 h.
Remove the HCl
Add approximately 1 ml of 0.1% Trypan blue and incubate the samples for 5 min at 96° C.
Remove the Trypan blue
Wash the samples in 50% acidic glycerol and mount the root sections between slide and cover slip.

The invention claimed is:

1. A method for promoting mycorrhizal symbiosis between a plant and a fungus, comprising a step of exogenously introducing a miPEP into the plant,
said miPEP being naturally present in said plant,
wherein the miPEP (i) is a peptide selected from the group consisting of SEQ ID NO: 2, SEQ ID NO: 6, SEQ ID NO: 10, and SEQ ID NO: 14, (ii) increases the accumulation of an miRNA in said plant relative to a plant that does not comprise exogenously introduced miPEP, and (iii) comprises or consists of an amino acid sequence of the natural miPEP encoded by the primary transcript of said miRNA; and
wherein said miRNA is selected from the group consisting of SEQ ID NO: 1, SEQ ID NO: 5, SEQ ID NO: 9, and SEQ ID NO: 13.

2. The method according to claim 1, wherein said miPEP is capable of modulating the accumulation of said miRNA in said plant, which miRNA regulates the expression of at least one gene involved in the mycorrhizal symbiosis in said plant,
said gene is involved in the mycorrhizal symbiosis encoding a transcription factor of the GRAS family,
said gene is involved in the mycorrhizal symbiosis being selected from the group consisting of: HAM1 and HAM2.

3. The method according to claim 1, wherein the mycorrhizal symbiosis is arbuscular mycorrhizal symbiosis.

4. The method according to claim 1, wherein the plant is a monocotyledon plant, a dicotyledon plant, a solanaceous plant, or a leguminous plant.

5. The method according to claim 1, wherein the plant is selected from the group consisting of: *Medicago truncatula*, *Medicago sativa* (alfalfa), *Solanum lycopersicum* (tomato), *Lotus japonicus* (birdsfoot trefoil), and *Oryza sativa* (rice).

6. The method according to claim 1, wherein the fungus is a glomeromycete, basidiomycete, or ascomycete.

7. The method according to claim 1, wherein the plant is a *Medicago truncatula* plant, the fungus is a glomeromycete fungus, and the miPEP is miPEP171b (SEQ ID NO: 2).

8. The method according to claim 1, wherein the plant is a *Solanum lycopersicum* plant, the fungus is a glomeromycete fungus, and the miPEP is slmiPEP171e (SEQ ID NO: 6).

9. The method according to claim 1, wherein the plant is a *Lotus japonicus* plant, the fungus is a glomeromycete fungus, and the miPEP is ljmiPEP171b (SEQ ID NO: 10).

10. The method according to claim 1, wherein the plant is an *Oryza sativa* plant, the fungus is a glomeromycete fungus, and the miPEP is osmiPEP171i (SEQ ID NO: 14).

11. The method according to claim 1, wherein:
(a) the miRNA comprises the nucleotide sequence of SEQ ID NO: 1, and the miPEP comprises the amino acid sequence of SEQ ID NO: 2;
(b) the miRNA comprises the nucleotide sequence of SEQ ID NO: 5, and the miPEP comprises the amino acid sequence of SEQ ID NO: 6;
(c) the miRNA comprises the nucleotide sequence of SEQ ID NO: 9, and the miPEP comprises the amino acid sequence SEQ ID NO: 10; or
(d) the miRNA comprises the nucleotide sequence of SEQ ID NO: 13, and the miPEP comprises the amino acid sequence of SEQ ID NO: 14,
wherein the fungus is a glomeromycete and the plant is a monocotyledon plant, a dicotyledon plant, a solanaceous plant or a leguminous plant.

12. The method according to claim 1, wherein the exogenous introduction comprises:
(a) administering to the plant of a composition comprising the miPEP at a concentration of $10^{-9}$ M to $10^{-4}$ M;
(b) administering to a grain or a seed of a composition comprising the miPEP at a concentration of $10^{-9}$ M to $10^{-4}$ M, and cultivating the grain or the seed to produce the plant; or
(c) administering to the plant a composition comprising a nucleic acid encoding the miPEP.

13. The method according to claim 12, wherein the administration comprises watering the plant with the composition, spraying the composition on the plant, or by adding a fertilizer comprising the composition to the plant.

14. The method according to claim 12, therein the concentration is selected from the group consisting of $10^{-9}$, $10^{-8}$, $10^{-7}$, $10^{-6}$, $10^{-5}$, and $10^{-4}$ M.

15. A method for the production of a transgenic plant comprising:
a) introducing a nucleic acid encoding a miPEP into a plant, or at least one cell of the plant, under conditions allowing the expression of the miPEP, and
b) growing the plant, or the at least one cell of said plant, obtained in step a) under conditions allowing a transgenic plant to be obtained,
wherein the miPEP (i) is a peptide selected from the group consisting of SEQ ID NO:2, SEQ ID NO: 6, SEQ ID NO:10 and SEQ ID NO:14, (ii) increases the accumulation of an miRNA in said plant relative to a plant that does not comprise exogenously introduced miPEP, and (iii) comprises or consists of an amino acid sequence of the natural miPEP encoded by the primary transcript of said miRNA; and wherein said miRNA is selected from the group consisting of SEQ ID NO: 1, SEQ ID NO: 5, SEQ ID NO: 9, and SEQ ID NO: 13 and the nucleic acid consists of the sequence coding for said miRNA.

16. A transgenic plant as obtained by method of claim 15.

* * * * *